(12) United States Patent
Hasan

(10) Patent No.: US 12,419,848 B2
(45) Date of Patent: Sep. 23, 2025

(54) TREATMENT OF HYPERINFLAMMATORY SYNDROME

(71) Applicant: REMICINE IP B.V., Velsen-Noord (BE)

(72) Inventor: Djohan Hasan, Kasterlee (BE)

(73) Assignee: REMICINE IP B.V., Velsen-Noord (NL)

( * ) Notice: Subject to any disclaimer, the term of this patent is extended or adjusted under 35 U.S.C. 154(b) by 446 days.

(21) Appl. No.: 17/907,640

(22) PCT Filed: Mar. 31, 2021

(86) PCT No.: PCT/NL2021/050208
§ 371 (c)(1),
(2) Date: Sep. 28, 2022

(87) PCT Pub. No.: WO2021/201680
PCT Pub. Date: Oct. 7, 2021

(65) Prior Publication Data
US 2023/0128348 A1    Apr. 27, 2023

(30) Foreign Application Priority Data

Mar. 31, 2020 (NL) ................................. 2025253
May 8, 2020 (NL) ................................. 2025541
Jan. 14, 2021 (NL) ................................. 2027321

(51) Int. Cl.
| | | |
|---|---|---|
| *A61K 31/167* | (2006.01) | |
| *A61K 9/00* | (2006.01) | |
| *A61P 1/04* | (2006.01) | |
| *A61P 3/10* | (2006.01) | |
| *A61P 5/00* | (2006.01) | |
| *A61P 9/10* | (2006.01) | |
| *A61P 11/00* | (2006.01) | |
| *A61P 13/10* | (2006.01) | |
| *A61P 15/00* | (2006.01) | |
| *A61P 17/06* | (2006.01) | |
| *A61P 19/02* | (2006.01) | |
| *A61P 21/04* | (2006.01) | |
| *A61P 25/08* | (2006.01) | |
| *A61P 25/16* | (2006.01) | |
| *A61P 25/28* | (2006.01) | |
| *A61P 29/00* | (2006.01) | |
| *A61P 31/04* | (2006.01) | |
| *A61P 31/14* | (2006.01) | |
| *A61P 35/00* | (2006.01) | |
| *A61P 37/06* | (2006.01) | |
| *A61P 37/08* | (2006.01) | |

(52) U.S. Cl.
CPC .......... *A61K 31/167* (2013.01); *A61K 9/0014* (2013.01); *A61K 9/0019* (2013.01); *A61K 9/0053* (2013.01); *A61K 9/006* (2013.01); *A61P 1/04* (2018.01); *A61P 3/10* (2018.01); *A61P 5/00* (2018.01); *A61P 9/10* (2018.01); *A61P 11/00* (2018.01); *A61P 13/10* (2018.01); *A61P 15/00* (2018.01); *A61P 17/06* (2018.01); *A61P 19/02* (2018.01); *A61P 21/04* (2018.01); *A61P 25/08* (2018.01); *A61P 25/16* (2018.01); *A61P 25/28* (2018.01); *A61P 29/00* (2018.01); *A61P 31/04* (2018.01); *A61P 31/14* (2018.01); *A61P 35/00* (2018.01); *A61P 37/06* (2018.01); *A61P 37/08* (2018.01)

(58) Field of Classification Search
CPC ................ A61K 9/0014; A61K 9/0019; A61K 9/0053; A61K 9/006; A61K 31/00; A61K 31/167; A61K 47/44; A61P 1/04; A61P 3/10; A61P 5/00; A61P 9/10; A61P 11/00; A61P 13/10; A61P 15/00; A61P 17/06; A61P 19/02; A61P 21/04; A61P 25/08; A61P 25/16; A61P 25/28; A61P 29/00; A61P 31/04; A61P 31/14; A61P 35/00; A61P 37/06; A61P 37/08
See application file for complete search history.

(56) References Cited

U.S. PATENT DOCUMENTS

2019/0133929 A1    5/2019  Koren et al.

FOREIGN PATENT DOCUMENTS

| DE | 19713263 A1 | * | 10/1998 | ........... A61K 31/245 |
|---|---|---|---|---|
| RU | 2558462 C | | 8/2015 | |
| WO | WO-9838998 A1 | * | 9/1998 | ........... A61K 31/445 |
| WO | 0200218 A2 | | 1/2002 | |
| WO | 2010122355 A1 | | 10/2010 | |
| WO | 2014155074 A1 | | 10/2014 | |

OTHER PUBLICATIONS

U.S. National Library of Medicine, "Impact of Intravenous Lidocaine on Clinical Outcomes of Patients With ARDS During COVID-19 Pandemia", Oct. 30, 2020 retrieved online <https://clinicaltrials.gov/ct2/show/NCT04609865>.

R.H. Sirait et al., "Lidocaine suppressed hyperinflammation in BALB/c mice model sterile injury via downregulation of toll-like receptor 4", Egyptian Journal of Anaesthesia 2018, vol. 34, pp. 135-137.

Z.A. Ali en R.S. El-Mallakh, "Nebulized Lidocaine in COVID-19, An Hypothesis", Medical Hypotheses, 2020, vol. 144, No. 109947, pp. 1-3.

(Continued)

*Primary Examiner* — Ali Soroush
(74) *Attorney, Agent, or Firm* — FisherBroyles, LLP; Roger L. Browdy

(57) ABSTRACT

Described is an antagonist of a mammalian P2X7R for use in the treatment of a hyperinflammatory syndrome in a mammalian patient, by primary lymph node targeted administration of the said P2X7R antagonist in the said patient to a concentration in the said targeted lymph nodes that is above the maximal tolerable plasma level of the said antagonist in the said mammal.

31 Claims, 4 Drawing Sheets

(56) References Cited

OTHER PUBLICATIONS

Figure 1A:
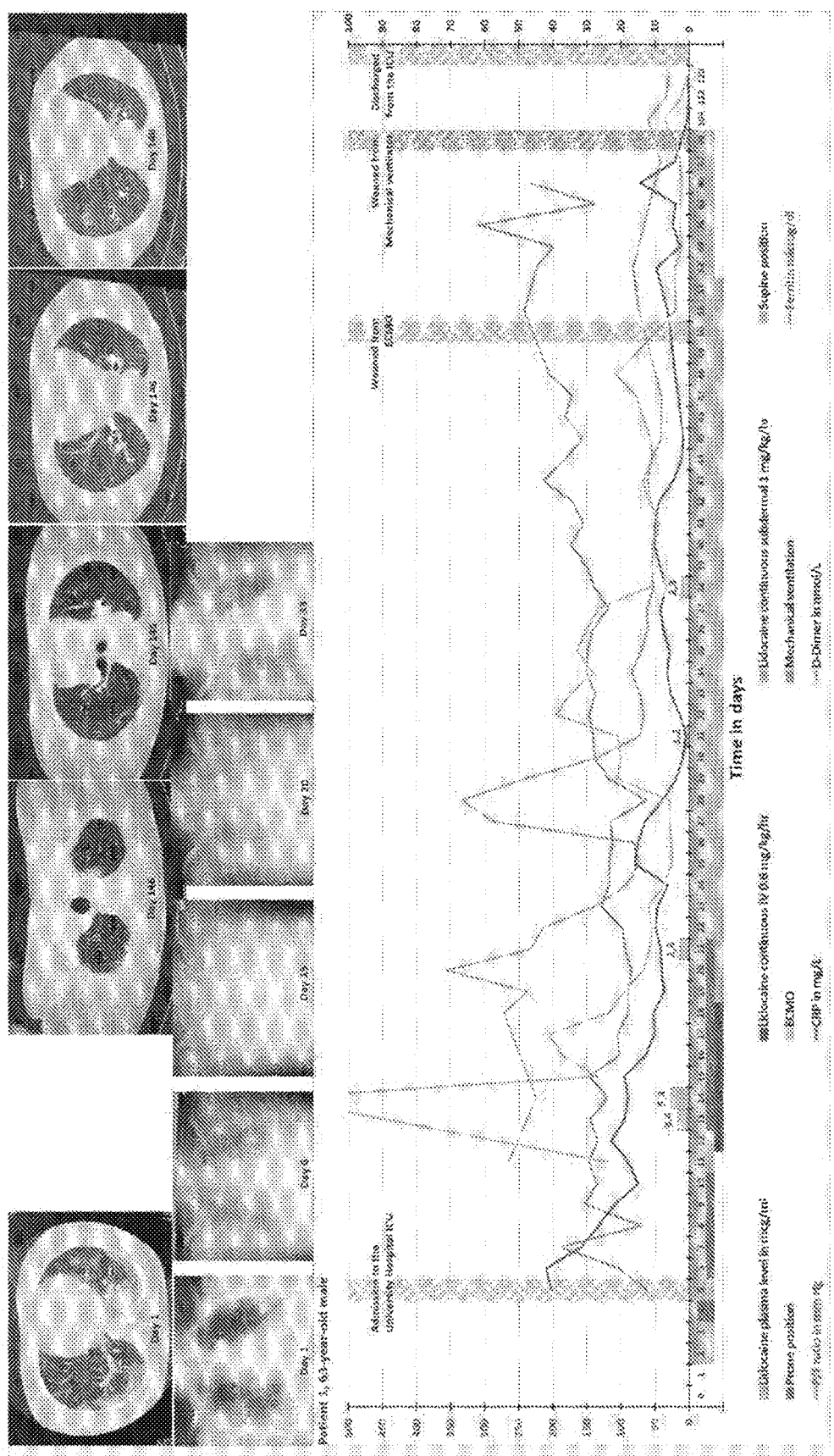

D. Kottke et al., "Development and evaluation of mucoadhesive buccal dosage forms of lidocaine hydrochloride by ex-vivo permeation studies", International Journal of Pharmaceuticals, 2020, vol. 581, nr. 119293, pp. 1-8.

D. Okura et al., "Lidocaine Preferentially Inhibits the Function of Purinergic P2X7 Receptors Expressed in Xenopus Docytes", Anesthesia & Analgesia 2015, vol. 120, No. 3, pp. 597-605.

Kahoru Nishina et al., "Intravenous Lidocaine Attenuates Acute Lung Injury Induced by Hydrochloric Acid Aspiration in Rabbits" Anesthesiology, Jan. 1, 1998, pp. 1300-1309, <URL:https://pubs.asahq.org/anesthesiology/article/88/5/1300/36802/Intravenous-Lidocaine-Attenuates-Acute-Lung-Injury>.

Tohru Ide et al: "The Effect of Epidural Anesthesia on Respiratory Distress Induced by Airway Occlusion in Isoflurane-Anesthetized Cats A", Anesth Analg, Jan. 1, 2001 pp. 749-754, <URL:https://journals.lww.com/anesthesia-analgesia/Fulltext/2001/03000/The Effect of Epidural Anesthesia on Respiratory .37.aspx>.

Dylan T Finnerty et al: "A novel role for lidocaine in COVID-19 patients?", British journal of anaesthesia : BJA, Jul. 23, 2020 (Jul. 23, 2020), pp. e391-e394, <URL:https://www.sciencedirect.com/science/article/pii/S000709122030578X?via%3Dihub>.

Xu Kaimei et al: "Effect of lidocaine on the safety of postoperative skin reconstruction after malignant melanoma resection", Experimental and Therapeutic Medicine, Apr. 23, 2019, pp. 949-954, <URL:https://www .ncbi.nlm.nih.gov/pmc/articles/PMC6639769/pdf/etm-18-02-0949.pdf>.

Razavi Bibi Marjan et al., "A review and new insights to antimicrobial action of local anesthetics", European Journal of Clinical Microbiology & Infectious Diseases, Springer, Wiesbaden, DE, vol. 38, no. Jan. 24, 2019. pp. 991-1002.

Mori Kenji et al: "Successful Management of Intractable Epilepsy with Lidocaine Tapes and Continuous Subcutaneous Lidocaine Infusion", EPILEPSIA, vol. 45, No. 10, Oct. 1, 2004, pp. 1287-1290.

Kodama S-I et al: "Lidocaine attenuates sepsis-induced diaphragmatic dysfunction in hamsters", Critical Care Medicine 2000 US, vol. 28, No. 7, 2000, pp. 2475-2479.

Garnock-Jones Karly Pet al: "Lidocaine 5% Medicated Plaster A Review of its Use in Postherpetic Neuralgia", Drugs, vol. 69, No. 15, 2009, pp. 2149-2165.

Burki et al: "Effects of airway anesthesia on dyspnea and ventilatory response to intravenous injection of adenosine in healthy human subjects", Pulmornary Pharmacology & Therapeutics Academic Press, GB, vol. 21, No. 1, Jan. 11, 2008, pp. 208-213.

T. K. Huang et al: "Surfactant Lavage with Lidocaine Improves Pulmonary Function in Piglets after HCI-Induced Acute Lung Injury", Lung, vol. 182, No. 1, Jan. 1, 2004, pp. 15-25.

Shannon Reagan-Shaw et al: "Dose translation from animal to human studies revisited", The FAS EB Journal, vol. 22, No. 3, Mar. 1, 2008, pp. 659-661.

"Tracheal Lidocaine Stops Airway Hyperresponsiveness ED— Hoekstra James; Qureshi Adnan", Annals of Emergency Medicine, vol. 25, No. 3, Mar. 1995.

Schenk Ursula et al: "ATP Inhibits the Generation and Function of Regulatory T Cells Through the Activation of Purinergic P2X Receptors", Science Signaling, vol. 4, No. 162, Mar. 1, 2011.

\* cited by examiner

TREATMENT OF HYPERINFLAMMATORY SYNDROME

The invention relates to an antagonist of a mammalian P2X7 receptor (P2X7R) for use in the treatment of a hyperinflammatory syndrome in a mammalian patient, by primary lymph node targeted administration of the said P2X7R antagonist in the said patient to a concentration in the said targeted lymph nodes that is above the maximal tolerable plasma level of the said antagonist in the said mammal.

BACKGROUND OF THE INVENTION

A hyperinflammatory syndrome, or hyperinflammation, is a known phenomenon in the medical art and is a symptom of a vast plurality of diseases resulting in dramatic if not lethal effects for the patient. The term 'hyperinflammation' as used herein is defined by the following 6 criteria (Webb et al., Lancet Rheumatol 2020, 2, (12) 754-763):
(1) Fever, defined as a temperature of more than 38.0° C.;
(2) Macrophage activation, defined as a ferritin concentration of 700 µg/l or more;
(3) Haematological dysfunction, defined as a neutrophil to lymphocyte ratio of 10 or more or both haemoglobin concentration of 9.2 g/dl or less and platelet count of $110 \times 10^9$ cells/L or less;
(4) Coagulopathy, defined as a D-dimer concentration of 1.5 µg/ml or more;
(5) Hepatic injury, defined as a lactate dehydrogenase concentration of 400 U/L or more, or an aspartate aminotransferase concentration of 100 U/L or more;
(6) Cytokinaemia, defined as an interleukin-6 concentration of 15 µg/ml or more, or a triglyceride concentration of 150 mg/dl or more, or a CRP concentration of 15 mg/dl or more.

Dyspnoea and pneumonia are common and abundant symptoms coinciding with hyperinflammation, in particular as a result of airways infections. A major event for hyperinflammation to occur is the release of intracellular ATP. The intercellular signalling by nucleotides (ATP, ADP, UTP and UDP) and nucleoside (adenosine) is known in the art as purinergic signalling.

Under normal resting conditions the extracellular levels of ATP are quite low at nanomolar concentrations (2-3 nM), whereas under specific conditions ATP release can rise by more than 1000-fold; such conditions may occur for the diseases as mentioned in the corresponding section 'diseases involving hyperinflammation' below, and include e.g. inflammation reactions, mechanical stress, surfactant release, membrane depolarisation, hypoxia.

In purinergic signalling, a plurality of receptors is known, for the ligand adenosine, also known as P1 receptors, and for nucleotide ligands, known as P2 receptors. The required extracellular concentrations of the ligand to reach an effect halfway between baseline and maximal effect (half maximal effective dose—$EC_{50}$) for adenosine is in the nanomolar range, whereas for ATP, UTP or ADP these concentrations range from 0.01 to 10 µM. All these receptors are known to be subject to desensitisation. Desensitisation of a receptor is defined as being unresponsive to activation by the ligand, resulting in zero transmembrane anion current. However, one of the P2 receptors, the P2X7R, is not prone to desensitisation, and the $EC_{50}$ for ATP to activate this receptor is much higher, namely at >1 mM. At such an ATP level, all other P1 and P2 purinergic receptors are fully desensitized.

By a disease as described above, such as a severe infection, massive extracellular ATP is released by the infected cells. This may be confined to the airway mucosa and the lung or may be extensive in multiple organs. The extracellular ATP has been observed to accumulate to 1.4 mM (Zhao et al., Front Immunol 2019, 10, 2524), resulting in the vigorous activation of the P2X7Rs causing hyperinflammation with massive pro-inflammatory immune response, massive pro-inflammatory and anti-inflammatory cytokine release and large pore formation with tissue cell destruction (Savio et al., Front Pharmacol 2018, 9, 52).

As a result of desensitisation of the P1 and P2 receptors, the physiological inflammatory response is deactivated (known as immune paralysis), rendering the patient susceptible to secondary infections.

Regulatory T-cells (Tregs) are key elements in the control of hyperinflammation, accelerating adenosine generation from extracellular ATP. Activation of P2X7Rs inhibits the suppressive potential and stability of Tregs.

The P2X7R plays an important role in many chronic and acute diseases. These diseases may be confined to 1 organ (Alzheimer's disease, multiple sclerosis, colitis) or may be diffusely disseminated as in bacterial sepsis or severe microbial infections, such as COVID-19, see also the below section 'diseases involving hyperinflammation'.

The current treatments of hyperinflammation are actually anti-inflammatory treatments. The drugs literally block the activation of the immune response by the inhibition of one or more pro-inflammatory pathways. These treatments undermine the physiological function of the pro-inflammatory immune response, namely, to recognise an "attack" by the invading microorganisms ("alarm phase") followed by the activation of the first line of defence (the innate immune system) and when required the activation of the adaptive immune system to specifically disarm the invader. Examples of such drug that hamper the inflammatory response of the patients are dexamethasone, baricitinib and anakinra.

Treatment of hyperinflammation has hitherto therefore been cumbersome. The present invention now provides a method for treatment of patients suffering from hyperinflammation without hampering the inflammatory response of the patients or at least to a much lesser extent.

It has been suggested in the art that the P2X7R could be a good candidate to target when treating hyperinflammation and concomitant dyspnoea and pneumonia. A P2X7R antagonist would block the vigorous activation of the P2X7Rs. Because a large proportion of the ATP release to the extracellular space is mediated by the P2X7Rs, antagonism thereof would result in the decrease of the extracellular ATP concentrations. This can potentially abrogate hyperinflammation and the concomitant immune paralysis. In addition, inhibition of P2X7Rs has been described to promote the cell-autonomous conversion of CD4+ T cells into Tregs after stimulation of their T-cell receptors (Schenk et al., Sci Signal 2011, 4 (162) ra12). Amelioration of hyperinflammation by P2X7R inhibition appears to be based on the increased activation and clonal expansion of the anti-inflammatory Tregs population.

Many P2X7R antagonists have been identified thus far (North and Jarvis, Mol Phar, 2013 (83) 759-769; Sluyter, Adv Exp Med Biol Prot Rev 2017 (19) 17-53). In order to achieve an effect, these antagonists have been administered systemically, in order to be transported by the blood to the envisaged site of action.

For example, CE-224,535 500 (Pfizer), AZD9056 (AstraZeneca) and JNJ54175446 (Johnson & Johnson) have been administered orally, however without great success. The anaesthetic lidocaine has been reported to be a P2X7R antagonist (Okura et al., *Anesth Analg* 2015, 120 (3), 597-605). Additional P2X7R antagonists are listed in the below section 'P2X7R antagonists'.

Although a P2X7R antagonist can abrogate hyperinflammation and restore the capacity of the immune system to combat secondary co-infections and improve the clinical condition in critically ill patients suffering from a severe airway infection, the problem with these compounds lie in the fact that in order to have an effect, the antagonist should bind the P2X7R to such an extent that the hyperinflammation and preferably the concomitant effects of e.g. dyspnoea are counteracted effectively. Such an effect may already be observed at a concentration of the receptor antagonist to inhibit the receptor for 10% (the so-called $IC_{10}$ value). The preferred inhibition is a 50% receptor inhibition, i.e. at the $IC_{50}$ value. However, for P2X7R antagonists, such a concentration is above the maximal tolerable plasma level of the said antagonist, i.e. resulting in undesired side effects such as anxiety, dizziness or even decreased spinal reflexes or worse. For example, the maximal tolerable plasma levels for lidocaine for humans are about 4.7 μg/ml, see table 1:

TABLE 1 maximal tolerable plasma level for lidocaine in humans

| Symptoms of toxic plasma levels of lidocaine | Lidocaine concentration | | |
|---|---|---|---|
| No noticeable symptoms | <0.020 | <20 | <4.69 |
| Anxiety, dizziness | 0.020 | 20 | 4.69 |
| Decreased spinal reflexes | 0.042 | 42 | 9.84 |
| Central nervous system (confusion, diplopia, nausea and vomiting, twitching and tremors, seizures with reduced consciousness, respiratory depression, coma, etc.) | 0.080 | 80 | 18.74 |
| Cardiac toxicity (bradycardia, hypotension, cardiovascular depression, cardiac arrest, etc.) | 0.130 | 130 | 30.46 |
| Cytotoxicity | 3.0 | 3000 | 702.9 |

For each P2X7R antagonist, the skilled person will be aware as how to determine the maximal tolerable plasma level.

However, P2X7R antagonists have not effectively been used for treatment of hyperinflammation, as in order to be effective, the systemic dose would exceed the maximal tolerable plasma level by far.

The present invention now provides P2X7R antagonists for use in the treatment of a hyperinflammatory syndrome in a mammalian patient, by primary lymph node targeted administration of the said P2X7R antagonist in the said patient to a concentration in the said targeted lymph nodes that is above the maximal tolerable plasma level of the said antagonist in the said mammal. By primary lymph node targeting, the envisaged $IC_x$ value can be obtained in the lymph nodes, while avoiding exceeding the maximal tolerable plasma level. The inventors have found that establishing the envisaged $IC_x$ value in lymph nodes results in effective treatment of hyperinflammation, and significantly relieves dyspnoea in patients suffering from severe airway infections, and other symptoms of hyperinflammation. Targeting lymph nodes was envisaged as it was contemplated that the lymphatic system is populated exclusively by trafficking immune cells, i.e. naïve T-cells, activated T-cells, B-cells, dendritic cells, monocytes, macrophages, neutrophils, mast cells, eosinophils, basophils and other immunologically relevant cells. It was found that by selective inhibition of the P2X7Rs of the immune cells of the lymphatic system by a P2X7R antagonist, clonal expansion of Tregs is induced. Subsequently, these Tregs migrate throughout the body exerting anti-inflammatory activity reducing systemic and (distant) local hyperinflammation.

The term 'primary lymph node targeted' refers to an administration or delivery route wherein the majority of the receptor antagonist is delivered directly from the administration site to the lymph node, while the effective amount of the said receptor antagonist in the plasma is at least 5 times, preferably at least 10 times or at least 15 times less than in the lymph node.

The antagonist is administered to a concentration in the targeted lymph nodes that corresponds to the $IC_x$ for the said receptor, the said $IC_x$ being above the maximal tolerable plasma level of the said antagonist in the said mammal, wherein x≥10, preferably 20, more preferably 30, even more preferably 40 and most preferably about 50. At $IC_{10}$, 10% receptor inhibition is observed, at $IC_{20}$, 20% receptor inhibition is observed, and so on. The higher x, the more receptor inhibition, the more effective the hyperinflammation is treated. It is clear to the skilled person that for a receptor antagonist that binds stronger to the receptor, the IC value will be lower than for a receptor antagonist that binds weaker to the receptor. The stronger the antagonist binds, the less amount of the said antagonist is needed to have the same effect as compared to a weaker binding antagonist. The IC-value is preferably determined as described in Okura, supra.

The skilled person will be aware of suitable delivery and administration routes for lymph node targeted administration. Preferred are topical and invasive administration. Invasive administration may not be suitable outside hospital settings. Therefore, it is very attractive to administer the receptor antagonist by topical administration. As a topical route, transmucosal and transdermal administration are preferred. In such a case, the antagonist is preferably administered in a lipophilic form, as a hydrophilic form would tend to be preferentially absorbed in the blood, resulting in undesired elevation of the plasma level of the receptor antagonist in the blood, and to less delivery in the lymph nodes. To this end, the receptor antagonist is preferably in the form of the free base thereof.

In a very attractive embodiment, the lymph node targeted administration comprises transmucosal administration in a body cavity covered with mucosa, preferably the said mucosa is close to one or more lymph nodes in order to enable fast and direct delivery. In particular, the oral cavity is suited for such administration. However, both nasal and al administration is also possible. With regard to nasal delivery, care has to be taken to preferably not inhale the receptor antagonist or to a minimal extent, as such inhalation may cause undesired elevation of the plasma level of the receptor antagonist. When administered to the oral cavity, the administration is preferably buccal, sublingual, pharyngeal or a combination thereof. The mucosa preferably has a low systemic permeability and are in close vicinity to lymph nodes. Permeability of different mucosal tissues is e.g. described in Goyal et al., *Nanomed Biotechnol* 2018, 46 (sup2), 539-551 and Lesch, et al., *J Dent Res* 1989, 68(9), 1345-1349.

It has been contemplated in the art that oral administration is inefficient route of drug delivery (Di Vergilio et al., *Br J Pharmacol* 2020). However, sublingual and buccal administration of the receptor antagonists, in particular lidocaine, has now been shown to be very effective without significantly elevating the antagonist level in the plasma. The permeability of the skin and mucosa to water, drugs, etc. is reported to be dependent on the site of the administration. For example, the permeability constant of the floor of the mouth (sublingual mucosa), lateral border of the tongue and buccal mucosa for tritium-labelled water is 22, 17 and 13 times as high as human skin, respectively. Moreover, the capacity of the submucosal capillaries to absorb molecules is much higher than the subcutaneous capillaries. Lidocaine hydrochloride is highly soluble in water (solubility of 680 mg/ml in water) and therefore will mainly be absorbed by the submucosal capillary. In contrast, the high lipophilic lidocaine base (solubility of 4 mg/ml in water, 760 mg/ml in 95% ethanol and 790 mg/ml in chloroform is preferably absorbed by the local initial lymphatics in the submucosal tissue (Gröningsson, et al., In *Analytical Profiles of Drug Substances*, Florey, K., Ed. Academic Press: 1985, Vol. 14, pp 207-243). In addition, the lymphatic drainage of the floor of the mouth is extensive, involving a large number of lymph nodes.

Sublingual and a buccal administration of lipophilic lidocaine base or of any other P2X7R antagonist is preferred. With a high concentration in a relatively low total dose the $IC_{50}$ of the P2X7Rs in the draining lymph nodes can be achieved to control systemic hyperinflammation and avoid toxic plasma levels of lidocaine or any other P2X7R antagonist. It is to be noted that sublingual and buccal administration of lipophilic lidocaine are different from oral administration of lidocaine. Oral administration of lidocaine is aimed at the resorption of the drug in the gastrointestinal tract, i.e. to systemic administration.

In another embodiment, the administration is transdermal and in the form of a cream, ointment or lotion, patch or plaster and/or involves microneedles or a combination thereof. For this type of administration, the receptor antagonist is preferably lipophilic for the same reason as described above. Transdermal administration of P2X7R antagonist, in particular in lipophilic from, an optionally in combination with skin penetration enhancers, such as alpha-terpineol, ethanol, lipid based nanoformulation can provide for convenient application.

In another embodiment, the administration is invasive, in particular chosen from intradermal, subdermal or subcutaneous administration. The dermal capillaries can transport substances from blood to tissue but the reabsorption of substances from tissue to blood is, if any, extremely low. Apparently, specialised initial lymphatics harbouring one way valve leaflets capable of absorbing fluid and molecules from the interstitium are localised in the dermis. The absorbed lymph fluid is then propelled forward in the lymphatic network by collecting lymphatic vessels harbouring a rhythmic contracting muscle layer. This system brings fluids and particles into the lymph nodes where numerous immune processes take place. The absorption of intradermal application into the lymph nodes appear to be 10 times slower than after deep subcutaneous application and leads to higher concentrations in the lymph nodes related to these lymphatic vessels. Smaller particles migrate more rapidly towards the lymphatic vessels and lymphatic nodes than larger particles. The route and rate of clearance after intradermal and subcutaneous administration in the back of the hand in humans resulted in clearance of the administered compounds after subcutaneous injection of 1%/min. and after intradermal injection of 8-10%/min.

The additional advantage is that the plasma concentrations of subcutaneously administered lidocaine are much lower than intravenously administered lidocaine. Intravenous administration of 2 mg/kg lidocaine in cats is almost immediately followed by a peak plasma concentration of 3.6 µg/mL (Thomasy et al., *Am J Vet Res* 2005, 66 (7), 1162-1166). In contrast, the achieved mean peak plasma concentrations after the subcutaneous administration of 30 mg/kg, 20 mg/kg and 10 mg/kg lidocaine are much lower: 1.69, 1.07 and 0.77 µg/mL, respectively (Hatef et al., *Aesthet Surg J* 209 (2), 122-128). The applied subcutaneous dose is 15, 10 and 5 times higher than the intravenous dose, respectively. The difference in the plasma concentrations after intravenous and subcutaneous administration of lidocaine is caused by the fact that, in contrast to the intravenous administration, a large proportion of the subcutaneously administered lidocaine is drained into the lymphatic system. This slows down the release of lidocaine to the venous blood.

Lymphatic absorption after intradermal administration is much higher than after deep subcutaneous administration. As intradermal infusion with lidocaine is not an accepted administration route for lidocaine, subdermal administration of lidocaine is proposed using a catheter inserted just beneath the dermis, that will result in higher concentrations of lidocaine in the draining local lymph nodes than a deep subcutaneous or intravenous infusion.

For invasive administration according to the invention, the receptor antagonist is preferably hydrophilic in particular in the form of a water soluble pharmaceutically acceptable salt thereof, such as the chloride salt.

In another embodiment, the administration is intravenous, the antagonist being lipophilic and confined in a drug delivery system avoiding direct release in the blood, e.g. by using nano-sized drug delivery systems, liposomes or polymer micelles. Oral administration of a P2X7R antagonist is also possible using delivery systems for intestinal lymphatic drug transport such as chylomicrons, etc, where delivery to the plasma is avoided. Intravenous administration at a low dosage where the maximum tolerable plasma level is not exceeded results in, if any, a much less pronounced effect. For lidocaine, an intravenous administration of 0.6 mg/kg/hr can be applied.

In particular, the P2X7R activation is activated by extracellular ATP. However, P2X7Rs can also be activated by membrane stretching, proteins from apoptotic cells, LL-37, cathelicidin and antimicrobial peptides. It is to be noted that all forms of such receptor activations are antagonised by the P2X7R antagonist.

In an attractive embodiment, the administration is an immediate release dosage form or a sustained release dosage form.

The administration preferably comprises one or more bolus administrations or comprises continuous administration or a combination thereof. A bolus is to be understood as the administration of a single tablet, pouch, injection, aerosol etc., or of a plurality thereof in any combination when administered subsequently without significant time intervals therebetween. It is also attractive to administer in a continuous fashion, e.g. as an infusion, or as a combination between one or more bolus administrations and a continuous administration.

In a particular embodiment, a bolus dosage corresponds with at least 1,000 times the amount of the receptor antagonist, that is comprised in 1 ml plasma at the maximal tolerable plasma level of the said antagonist, preferably at least 5,000 times, more preferably at least 10,000 times. Is means that according to this embodiment, the bolus is defined by amount of the receptor antagonist that is present in 1 ml plasma at the maximum tolerable plasma level. For example, the maximal tolerable plasma level of lidocaine in humans is 4, 7 µg/ml. this would mean that the bolus would be at least 1,000 times 4,7 µg, i.e. 4.7 mg.

The bolus is preferably administered 2-10 times daily.

The antagonist is preferably administered in a liquid medium comprising at least 1 w/v % of the receptor antagonist, preferably at least 5 w/v % and most preferably at least 10 w/v %. Such high concentrations of receptor antagonist, in particular of lidocaine have hitherto not been used in the art. Such concentrations, when used according to the art, i.e. directed to systemic delivery via the blood would lead to unacceptably high plasma levels of beyond the maximal tolerable plasma level of the said antagonist. For example, in order to treat hyperinflammation and concomitant dyspnoea in a patient suffering from severe airways infection e.g. by infection by SARS-CoV-2.

When it comes to invasive administration, the lymph node targeted administration is preferably by continuous intradermal, subdermal or subcutaneous infusion. In particular patients that are intubated for ventilation and/or kept in coma may need such administration route.

For administration by a continuous infusion, the dosage preferably corresponds with at least 10 times the $IC_{10}$ value per kg body weight per hour, more preferably at least 10 times the $IC_{20}$ value per kg body weight per hour, even more preferably at least 10 times the $IC_{30}$ value per kg body weight per hour, still even more preferably at least 10 times the $IC_{40}$ value per kg body weight per hour, at most preferably least times the $IC_{50}$ value per kg body weight per hour, at least 10 times the $IC_{10}$ value per kg body weight per hour, at least 10 times the $IC_{10}$ value per kg body weight per hour. More preferably the dosage is at least times the $IC_{50}$ value per kg body weight per hour. For lidocaine, the latter value would correspond with about 1 mg/kg/hr. The $IC_{50}$ value for lidocaine is 66 μg/ml (0.066×15=0.99).

According to a very attractive embodiment, the treatment involves a hyperinflammatory syndrome of a disease, chosen from the group, consisting of autoimmune diseases and immune-related diseases such as asthma, allergy and chronic pulmonary disease; treatment-induced immune-related diseases, such as chemotherapy; infectious diseases, such as viral and bacterial infections; cardiovascular diseases and neurovascular diseases; neuroinflammatory and neurodegenerative diseases; epileptic disorders; affective disorders and psychiatric syndromes; fibrosis; cancer-related disorders; tumour pseudoprogression; cancer and neoplasms; trauma and posttraumatic syndromes; post-organ transplantation syndromes including transplanted organ rejection. However, the treatment can involve any disease wherein the P2X7R activation plays a role and wherein the disease can be treated by a P2X7R antagonist. These diseases are listed in the section 'diseases involving hyperinflammation' below.

The hyperinflammatory syndrome preferably includes dyspnoea, in particular, the dyspnoea is associated with a viral infection, bacterial infection, carcinomas, chronic obstructive pulmonary disease (COPD), asthma, allergy, chemotherapy. The viral infection is particularly caused by a virus, chosen from the group, consisting of Corona, in particular SARS-CoV-2; Influenza; Ebola; Respiratory Syncytial Virus; HIV.

The P2X7R antagonist is preferably chosen from the group, consisting of: aminoamide derivatives, in particular lidocaine, bupivacaine, ropivacaine and mepivacaine; antibodies against P2X7Rs, in particular monoclonal antibodies, amino ester derivatives, in particular benzocaine and procaine; adamantane amide derivatives; triazole derivatives; diarylimidazolidine derivatives; pyroglutamic acid amide derivatives; pyrazole acetamide derivatives; dihydrodibenzo[a,g]quinolizinium derivatives; tetrazole derivatives; tyrosine based derivatives; pyrazolodiazepine derivatives; imidazoles derivatives; benzamides derivatives, KN62 analogues and derivatives; adamantane carboxamides; aryl carbohydrazides; cyanoguanidines; aryltetrazoles and aryltriazoles; PPADS tetrasodium salt; brilliant blue G (BBG); oxidised ATP (o-ATP); massadine; stylissadine A and B; P2X7R inhibitors C23, C40 and C60; [3H]A-804598 ([3H]2-cyano-1-[(1S)-1-phenylethyl]-3-quinolin-5-ylguanidine); bicycloheteroaryl compounds. However, additional suitable P2X7R antagonists are given in the below section 'P2X7R antagonists'.

In a very attractive embodiment, the P2X7R antagonist comprises lidocaine. Lidocaine has been shown very effective in treatment of hyperinflammation. The lidocaine is preferably administered topically, preferably in the free base form. The administration is preferably in the oral cavity. The lidocaine base is preferably administered in a liquid medium comprising at least 2.5 w/v % of the receptor antagonist, preferably at least 5 w/v %, more preferably at least 10 w/v %. Such a liquid medium can e.g. be ethanol-based.

In another attractive embodiment, the treatment comprises invasive administration of lidocaine in a water-soluble salt form, in particular lidocaine-HCl. The lidocaine salt is preferably administered intradermally, subdermally or subcutaneously. The lidocaine salt is preferably administered by continuous intradermal, subdermal or subcutaneous infusion.

The mammalian patient is preferably a human patient but can be any mammal suffering from a disease mediated by P2X7R activation.

The invention will now be further illustrated by way of the following FIGURES and examples.

FIG. 1 *a-f* shows six cases with severe COVID-19 treated with subdermal lidocaine. All patients are COVID-19 cases with a positive COVID-19 test. Two patients were treated with mechanical ventilation and extracorporeal membrane oxygenation (ECMO) and 4 patients were treated with mechanical ventilators only. The maximal intravenous lidocaine dose is 0.6 mg/kg/hour and the maximal subdermal lidocaine dose is 1 mg/kg/hour. All patients recovered completely from their illness.

FIG. 1*a*: A 63-year-old male (example 1) with COVID-19-induced ARDS, was admitted to the hospital. The CT scan showed bilateral ground glass opacities. Co-morbidities: COPD, smoking 60 cigarettes per day for more than 40 years. About 40 years before admission the patient suffered from pneumothorax. After admission the clinical condition deteriorated requiring an ICU admission and mechanical ventilation on day 4. On Day 11 continuous intravenous lidocaine of 0.6 mg/kg/hr was initiated but the patient's condition kept worsening with high pulmonary artery pressures and reduced aeration of the lung. On day 19 the continuous intravenous lidocaine of 0.6 mg/kg/hr was changed to continuous subdermal lidocaine of 1 mg/kg/hr. This was followed by improvement of the clinical condition and on day the aeration of the lung was improved but the pulmonary artery pressures remain high. Despite this the P/F ratio was gradually improving and ECMO weaning was done on day 50. No new ECG changes were observed during treatment with lidocaine. Blood metHb were within the normal range (0.3-0.8%).

Figure 1B:
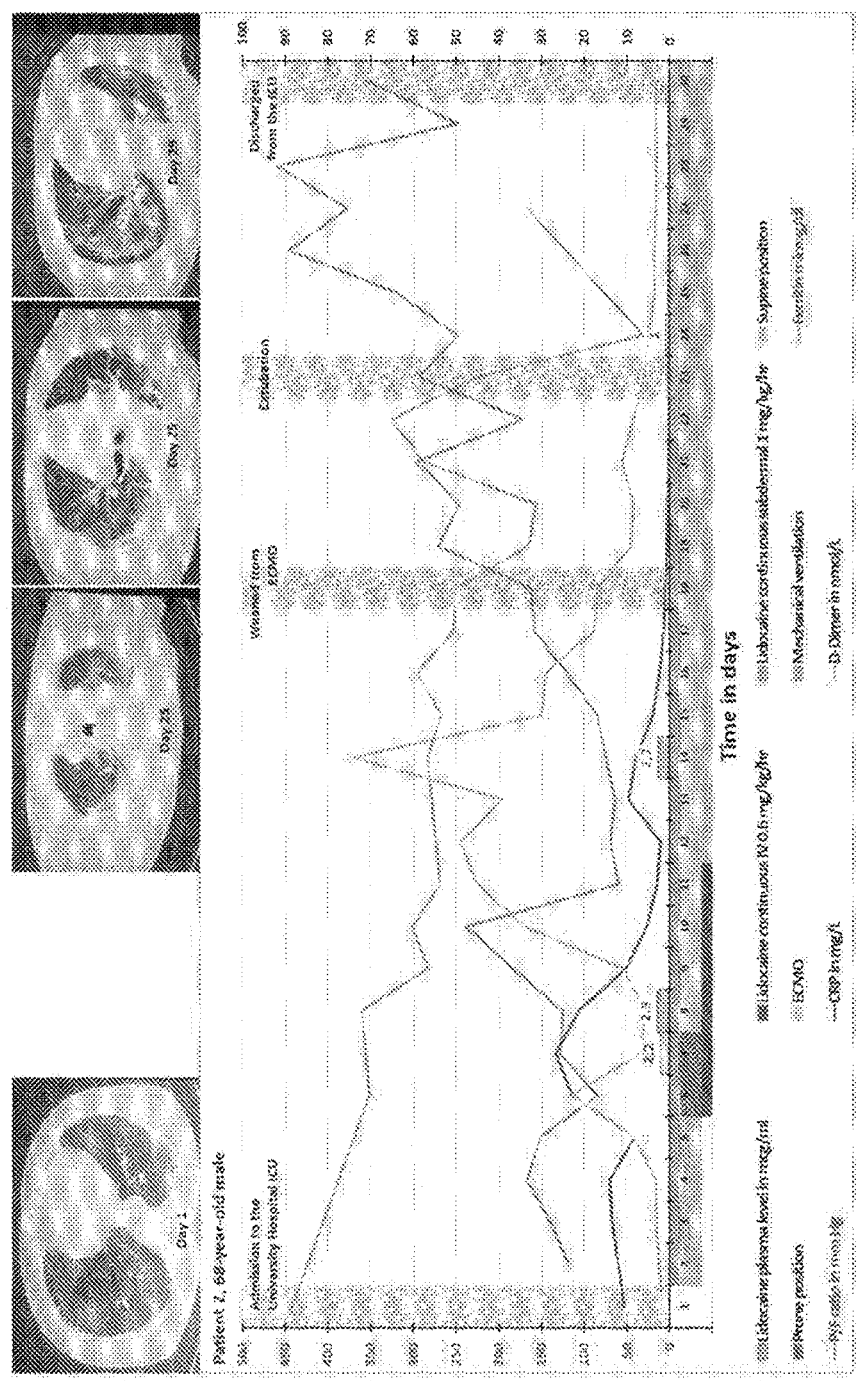

FIG. 1*b*: A 68-year-old male with COVID-19-induced ARDS (example 2) admitted to the ICU and required mechanical ventilation. The CT scan showed bilateral ground glass opacities. Co-morbidity: Asthma. After admission the patient's condition was deteriorating. On Day 5 continuous intravenous lidocaine of 0.6 mg/kg/hr was initiated, but the clinical condition and the P/F ratio kept worsening. On Day 11 the intravenous lidocaine of 0.6 mg/kg/hr was changed to continuous subdermal lidocaine of 1 mg/kg/hr. A few days later this was followed by improvement of the clinical condition and the P/F ratio. No new ECG changes were observed during treatment with lidocaine. Blood metHb were within the normal range (0.1-0.6%).

Figures 1C, 1D:
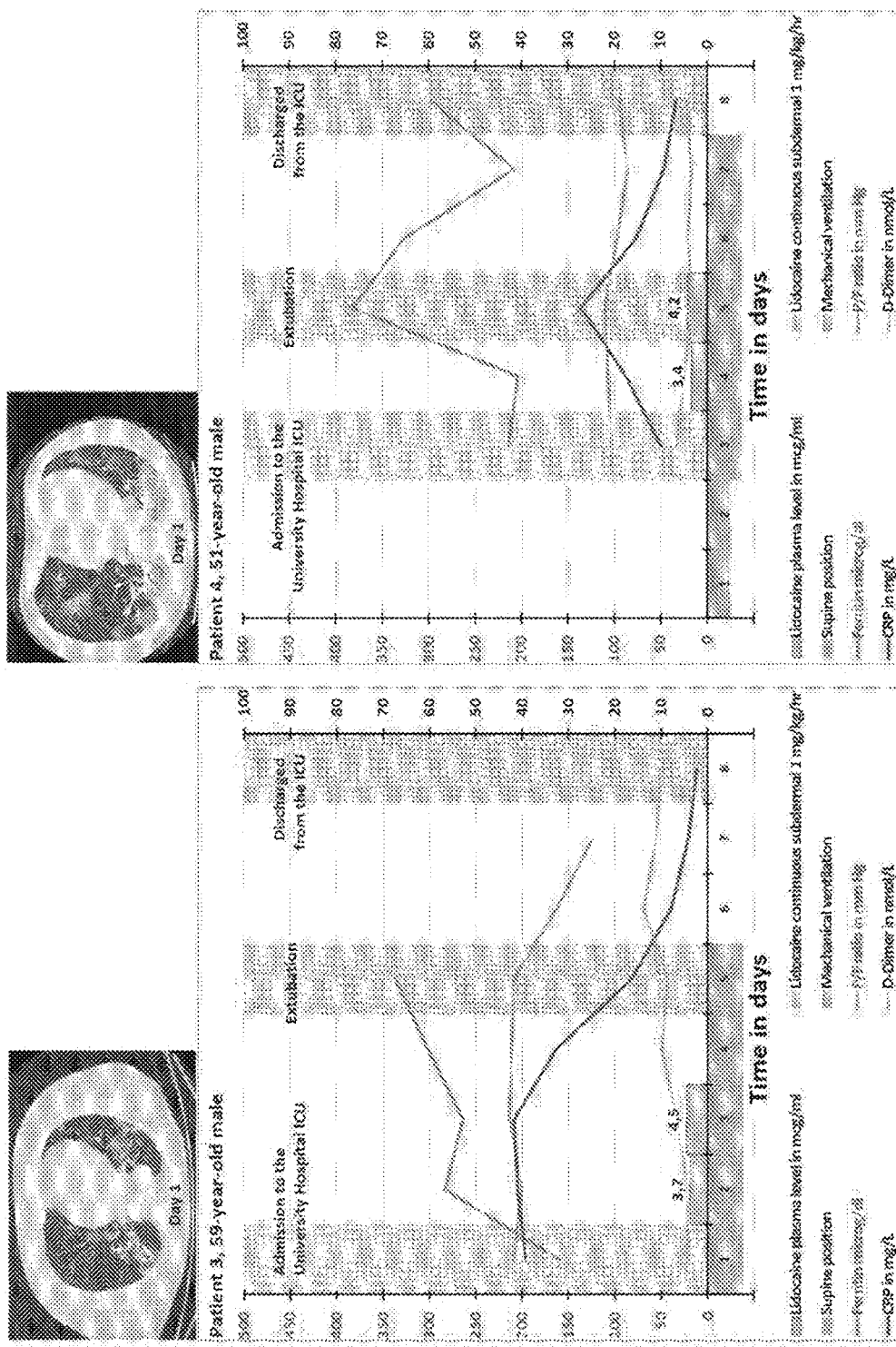

FIG. 1c: A 59-year-old male (example 3) with respiratory distress and bilateral ground glass opacities on the CT scan. Co-morbidity: diabetes mellitus and gout. No new ECG changes were observed during treatment with lidocaine. Blood MetHb were within the normal range (0.1-0.4%).

FIG. 1d: A 51-year-old male with fever, dyspnoea and cough due to COVID-19 (example 4). The CT scan showed bilateral ground glass opacities. Co-morbidity: none. No new ECG changes were observed during treatment with lidocaine. Blood metHb were within the normal range (0.1-0.3%).

Figures 1E, 1F:
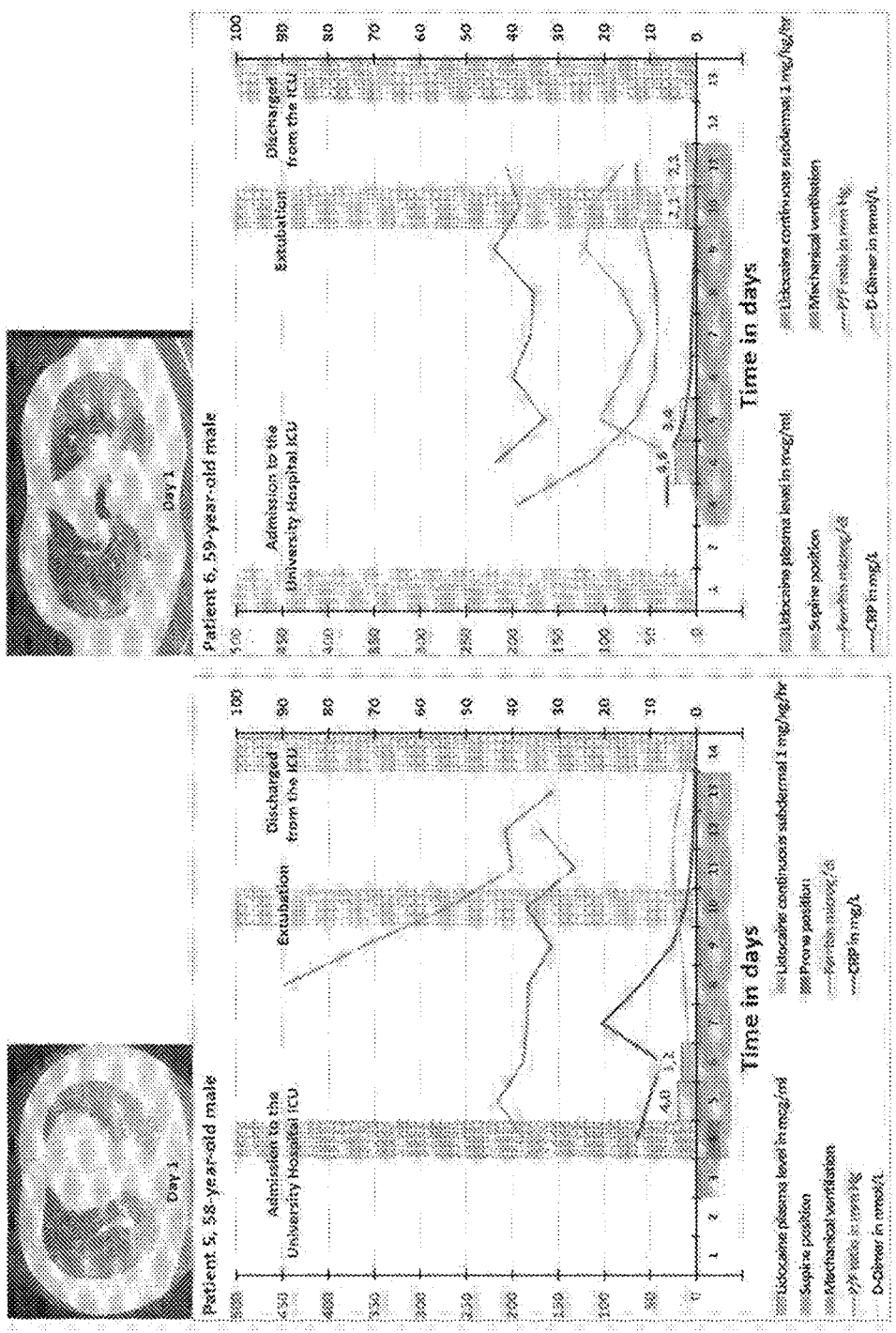

FIG. 1e: A 58-year-old male with fever, dyspnoea and cough due to COVID-19 (example 5). The CT scan showed bilateral ground glass opacities. Co-morbidity: Fatty liver. No new ECG changes were observed during treatment with lidocaine. Blood metHb were within the normal range (0.1-0.3%).

FIG. 1f: A 59-year-old male with fever, dyspnoea and cough due to COVID-19 (example 6). CT scan showed bilateral ground glass opacities. Co-morbidity: Hypertension on medication. No new ECG changes were observed during treatment with lidocaine. MetHb were within the normal range (0.1-0.3%).

EXAMPLES 1-6

From April 2020 until end of July 2020, 6 critically ill patients with COVID-19 admitted to the hospital and with intravenous and subdermal continuous infusion of lidocaine. This treatment was initiated on the basis of compassionate use. The concentration of the lidocaine infusion solution is 20 mg/ml (2%). The lidocaine treatment in the first 2 patients was initiated intravenously, the administration route for continuous administration of lidocaine commonly used in daily practice. The dose for intravenous administration is 0.6 mg/kg/hr. Due to the limited efficacy of intravenous lidocaine and based on the hypothesis of selectively targeting the inhibition of the P2X7Rs of the immune cells, the infusion in both patients was converted to subdermal infusion of 1.0 mg/kg/hr after 7 and 6 days, respectively. The other 4 patients were treated with subdermal infusion only. The time course of clinical parameters of these 6 patients is presented in FIGS. 1a-f.

Patient 1—Example 1

The first patient, a 63-year-old male (75 kg, 168 cm), developed fever and nausea on Mar. 27, 2020 and three days later he started to cough and became dyspnoeic. After 5 days the PCR COVID-19 test was positive and he was admitted to the hospital with COVID-19-induced ARDS. Co-morbidities: COPD, smoking 60 cigarettes per day for more than 40 years. About 40 years earlier the patient suffered from pneumothorax. On day 3 the patient deteriorated and was intubated and mechanically ventilated due to poor blood gases. No haemodynamic instability was observed. The CT scan showed bilateral ground glass opacities compatible with ARDS. On day 5 the patient was transferred to the ICU of the University Hospital because of further respiratory deterioration. Prone position mechanical ventilation was initiated due to the progression of the respiratory disease with an extremely low $PaO_2/FiO_2$ ratio of 63.3 mm Hg (severe ARDS according to the Berlin definition. The Berlin definition of ARDS includes severe $PaO_2/FiO_2$ ratio:100 mm Hg, moderate $PaO_2/FiO_2$ 100 to ≤200 mm Hg, mild PaO2/FiO2 200 to ≤300 mm Hg, no ARDS $PaO_2/FiO2$>300 mm Hg [361]). The initial ventilator settings: APRV, $P_{high}$27 cm $H_2O$, $T_{high}$ 7.0 S, Plow 0 cm $H_2O$, $T_{low}$ 0.32 s. The $PaCO_2$ was normal. The echocardiographic estimated pulmonary arterial systolic pressure (PASP) was 80 mm Hg. The Krebs von Lungen 6 (KL-6, a marker for lung fibrosis [362]) plasma level was highly elevated (1299 U/mL; normal value<425 U/mL), CRP was also high (40.4 mg/L; normal value<10 mg/L) and albumin was 2.2 g/dl. The white blood cell count, platelet count and urine production were normal. On day 4 the chest X-ray was not improved. On day 6 the $PaO_2/FiO_2$ ratio was slightly increased but remained low at 103 mm Hg and the chest X-ray showed progression of the ARDS. ECMO was initiated due to exhausted ventilatory strategy. On day 9 the $PaO_2/FiO_2$ ratio improved but remained low at around 153 mm Hg but the CRP declined to around 21.8 mg/L. The patient was put on muscle relaxants. The patient's ARDS status had improved from severe to moderate ARDS. From day 10 until day 30 the ferritin levels were well>1000 ng/ml (>100 g/dl). From day 11 until day 62 D-Dimer was very high reaching 121.9 nM/L day 14. On day 11 no improvement of the blood gases was observed and it was decided to treat the patient with continuous intravenous lidocaine 0.6 mg/kg/hr. On day 16 CRP showed a progressive decline from 19 (on day 12) to 12.8 (on day 16) and 7.4 (on day 19) but the $PaO_2/FiO_2$ ratio remained poor at around 90 mm Hg (severe ARDS according to the Berlin criteria) and the chest X-ray image on day 15, 3 days after the initiation of the intravenous lidocaine infusion, deteriorated dramatically. The lidocaine plasma concentrations were 3.4 µg/ml on day 13 and 5.4 µg/ml on day 14. On day 19 the continuous intravenous lidocaine infusion was replaced by continuous subdermal lidocaine infusion of 1 mg/kg/hr. Although the $PaO_2/FiO_2$ ratio remained unchanged on day 20 (1 day after the switch to the continuous subdermal lidocaine) the chest X-ray improved clearly. On day 21 the lidocaine plasma concentration was 2.6 □g/ml, albumin was 2.5 g/dl. From day 22 on the $PaO_2/FiO_2$ ratio was gradually improving reaching 151 mm Hg on day 34 (moderate ARDS). The KL-6 on day 22 dropped to 458 U/L (this is only slightly above the normal value of <450 U/l). On day 31 The CRP was low at 1 mg/L and the lidocaine plasma concentration was 1.2 □g/ml. The muscle relaxants were discontinued. Albumin was 2.3 g/dl. On day 33 the chest X-ray was further improved and the CRP remained low at 5.5 mg/L. The patient was awake and could communicate with the nurses. On day 38 the lidocaine plasma level was 2.3. On Day 43 the $PaO_2/FiO_2$ ratio was increased to 214 mm Hg. According to the Berlin definition of ARDS [361], the patient's ARDS status had changed from moderate to mild. Albumin was 2.8 g/dl. On day 50 the patient was weaned from ECMO. On day 51 the patient underwent tracheotomy. Because the clinical condition of the patient was stabilised with a low CRP of 6.3 mg/L on day 55, the continuous subdermal lidocaine was discontinued on day 57. On day 69 he developed pneumothorax requiring pleural drainage. On day 99 he was weaned from the mechanical ventilator and was discharged from the ICU on day 121. The patient received Favipiravir for 14 days. No new ECG changes were observed during treatment with lidocaine. Blood metHb were within the normal range (0.3-0.8%). The patient was discharged from the hospital on day 187, he went home, he could walk but needed extra oxygen supply of 2 L/min. Nine months after admission the patient is doing well and has returned to work.

Patient 2—Example 2

The second patient is a 68-year-old male with COVID-19-induced ARDS and positive PCR test admitted to the hospital. Co-morbidity: Asthma. The CT scan showed bilateral ground glass opacities. Haemodynamically the patient was stable. On day 2 the respiratory conditions deteriorated, the $PaO_2/FiO2$ ratio is 118 mm Hg (moderate ARDS according to the Berlin ARDS definition [361]). The patient was intubated and required mechanical ventilation. The initial ventilator settings: Pressure control, peak inspiratory pressure 28 cm $H_2O$, PEEP 13 cm $H_2O$, respiratory rate 30/min. CRP was 10.6 mg/L and KL-6 was 486 U/ml. White blood cell count, platelet count and urine production were normal. The ferritin levels remained >1000 ng/ml (100 μg/dl) during the entire ICU stay. Albumin was 2.9 g/dl. The following 3 days the $PaO_2/FiO_2$ ratio improved to around 150 mm Hg. The $PaO_2/FiO_2$ ratio dropped from 152 mm Hg on day to 84 mm Hg on Day 6. CRP was increased to 22.9 and the KL-6 was increased to 762 U/ml. The patient was put in prone position and given muscle relaxants. Continuous intravenous lidocaine of 0.6 ml/kg/hr was started. Albumin was 1.8 g/dl. On day 7 the $PaO_2/FiO_2$ ratio increased to 128 mm Hg, CRP dropped to 10.3 mg/mL and the lidocaine plasma concentration was 2.2 μg/ml. From day 3 until discharge from the ICU D-Dimer values were elevated reaching 75 nM/L on day 14. On day 8, although the $PaO_2/FiO2$ ratio improved from 84 to 125 mm Hg, the mechanical ventilatory strategies were exhausted and the patient was put on ECMO. The KL-6 was increased to 845 U/L and lidocaine plasma level was 2.9 μg/ml. The $PaO_2/FiO_2$ ratio improved to 238 mm Hg on day 9 but on day 10 a sharp drop of the $PaO_2/FiO_2$ ratio to 60 mm Hg was observed and CRP was 2.0 mg/ml. The patient's ARDS status had changed from moderate to severe according to the Berlin ARDS criteria (Ranieri et al., *Jama* 2020, 307 (23), 252-2533). Lidocaine treatment was switched from continuous intravenous to continuous subdermal (dosage: 1 mg/kg/hr). On day 14 the lidocaine plasma level was 2.7 μg/ml. KL-6 dropped to 549 U/l. On day 17 the clinical condition of the patient was improving and the $PaO_2/FiO_2$ ratio reached 158 mm Hg. The patient was weaned from ECMO. The $PaO_2/FiO_2$ ratio improved further reaching 291 mm Hg on day 21 and the patient's ARDS status has changed from moderate to mild ARDS (Ranieri, supra). On Day 22 mechanical ventilation was discontinued and the patient was extubated. The patient was orientated, no signs of confusion were detected. Lidocaine treatment was continued until discharge from the ICU on Day 30. The patient received Tocilizumab on day 8 and Favipiravir for 14 days. No new ECG changes were observed during treatment with lidocaine. Blood metHb were within the normal range (0.1-0.6%). At 3 months after admission the patient is doing well.

Patient 3—Example 3

The third patient, a 59-year-old male, was admitted to the hospital with respiratory distress and bilateral ground glass opacities on the CT scan. Co-morbidities: Diabetes mellitus and gout. The patient required immediate intubation and mechanical ventilation. The initial ventilator settings: Pressure control, peak inspiratory pressure 30 cm $H_2O$, PEEP 15 cm $H_2O$, respiratory rate 25/min. The $PaO_2/FiO_2$ ratio on admission was 160 mm Hg (moderate ARDS according to the Berlin definition [361]), CRP was 39.3 mg/L and KL-6 was 294 U/ml. White blood cell count was increased 13.10-9/L, platelet count and urine production were normal. Albumin was 2.1 g/dl. Haemodynamic parameters were stable. On the admission day continuous subdermal lidocaine was started at 1 mg/kg/hr. On day 2 the $PaO_2/FiO_2$ ratio improved to 283 mm Hg and the patient's ARDS status had changed from moderate to mild ARDS. CRP was 41 mg/L, KL-6 was 268 U/l and the lidocaine plasma level was 3.7 μg/ml. Albumin was 1.7 g/dl. On day 4 the $PaO_2/FiO_2$ ratio was 302 mm Hg, the patient's ARDS status had changed from mild ARDS to no ARDS according to the Berlin ARDS criteria. On day 5 the $PaO_2/FiO_2$ ratio was improved further to 328 mm Hg and CRP dropped to 16.4 and the patient was extubated. The patient was orientated, no signs of confusion were detected. The patient was discharged from the ICU on day 8, CRP was 2.3 mg/ml. Albumin was 2.5 g/dl. The patient received Tocilizumab on day 3 and Favipiravir for 15 days. No new ECG changes were observed during treatment with lidocaine. Blood MetHb were within the normal range (0.1-0.4%). The patient was discharged home on day 20. After 3 months he is doing well.

Patient 4—Example 4

The fourth patient is a 51-year-old male. Ten days before admission he developed fever and 2 days before admission dyspnoea and coughing. On the day of admission, the PCR COVID-19 test was positive. The CT scan showed bilateral ground glass opacities. Co-morbidity: none. The patient was intubated and put on mechanical ventilation on admission. On day 3 he was transferred to the University Hospital because of deterioration of pulmonary condition. The initial ventilator settings: Pressure control, peak inspiratory pressure 24 cm $H_2O$, PEEP 12 cm $H_2O$, respiratory rate 15/min. The haemodynamic conditions were stable. White blood cell count and platelet count were normal. Albumin was 2.6 g/dl. Continuous subdermal lidocaine was started immediately. On day 3 the $PaO_2/FiO_2$ ratio was 214 (moderate ARDS according to the Berlin definition [361]). KL-6 was 177 U/L and CRP was 17.4 mg/L. On day 5 the $PaO_2/FiO_2$ ratio was increased to 382 (the patient's ARDS status had changed from mild ARDS to no ARDS) and lidocaine plasma concentration was 5.2 μg/ml. CRP was 27.3 mg/L. Lidocaine plasma levels on day 3 and 4 were 3.4 and 4.2 μg/ml, respectively. KL-6 was 163 U/L. The patient was extubated. The patient was orientated, no signs of confusion were detected. The patient was discharged from the ICU on day 8, the CRP was 9.3 mg/L. The patient received Favipiravir for 14 days. No new ECG changes were observed during treatment with lidocaine. Blood metHb were within the normal range (0.1-0.3%). He was discharged home on day 28. At 3 months he is doing well and has returned to work.

Patient 5—Example 5

The fifth patient is a 58-year-old male. Nine days before admission he developed a sore throat. A day later he developed fever. Two days before admission he started coughing and was dyspnoeic. On the day of admission the PCR COVID-19 test was positive. The CT scan showed bilateral ground glass opacities. Co-morbidity: Fatty liver. The patient was initially admitted to the hospital ward. On day 3 the patient deteriorated and had to be intubated and put on mechanical ventilation. On day 4 the patient was transferred to the University Hospital due to deterioration of the pulmonary condition. The initial ventilator settings: Pressure control, peak inspiratory pressure 27 cm $H_2O$, PEEP 12 cm $H_2O$, respiratory rate 25/min. $PaO_2/FiO_2$ ratio was 188 (moderate ARDS according to the Berlin definition). Haemodynamic parameters were stable and CRP was 12.9 mg/ml. White blood cell count was increased ($14.4.10^{91}$/L) but platelet count was normal. KL-6 was 330 U/L. Continuous subdermal lidocaine was started at 1 mg/kg/hr. Albumin was 2.8 g/dl. On day 5 the $PaO_2/FiO_2$ ratio was unchanged, CRP was 10.4 mg/L and the lidocaine plasma level was 4 µg/ml. On day 6 the lidocaine plasma level was 3.2 µg/ml. KL-6 remained stable at 400 U/L. Albumin was 2.3 g/dl. On day 10 the respiratory insufficiency had cleared, although the $PaO_2/FiO2$ ratio remained 184 the CRP dropped to 2.4 mg/L and KL-6 was 322 U/L. The patient was extubated and he was orientated, no signs of confusion were detected. On day 14 the patient was discharged from the ICU. The patient received Tocilizumab on day 7 and Favipiravir for 10 days. No new ECG changes were observed during treatment with lidocaine. Blood metHb were within the normal range (0.1-0.3%). On day 20 the patient was discharged home and is doing well at 3 months after admission.

Patient 6—Example 16

The sixth patient is a 59-year-old male with fever, dyspnoea and cough due to COVID-19. CT scan showed bilateral ground glass opacities. Co-morbidity: Hypertension on medication. The patient was admitted to the general ward. KL-6 233 U/L, white blood cell count and platelet count were normal. Albumin was 3.6 g/dl. On day 3 there is a deterioration of the respiratory function necessitating a transfer to the ICU and mechanical ventilation. The initial ventilator settings: Pressure control, peak inspiratory pressure 22 cm $H_2O$, PEEP 10 cm $H_2O$, respiratory rate 20/min. Continuous subdermal lidocaine of 1 mg/kg/hr was initiated after admission to the ICU. Haemodynamic parameters were stable. CRP was 6.3 mg/L, KL-6 was 263 U/L. On day 4 a progressive respiratory failure occurred requiring intubation and mechanical ventilation. $PaO_2/FiO_2$ ratio was 218 mm Hg, the haemodynamic parameters remained stable. CRP was 6.3 mg/L, the white blood count and platelet count were normal. Lidocaine plasma level was 4.6 µg/ml. On day 5 the $PaO_2/FiO_2$ ratio dropped further to 164 mm Hg. Lidocaine plasma level was 3.4 µg/ml. Albumin was 3.2 g/dl. On day 9 the clinical condition of the patient improved. The ventilator settings could be decreased, the $PaO_2/FiO_2$ ratio remained 207 mm Hg during the weaning period, CRP was 0.7 mg/L. On day 10 the patient was extubated, he was orientated, no signs of confusion were detected. On day 13 the patient was discharged from the ICU. Tocilizumab was given on day 4. The patient received Favipiravir for 11 days. No new ECG changes were observed during treatment with lidocaine. Blood metHb were within the normal range (0.1-0.3%). He was discharged from the hospital on day 20 and at 3 months after admission he is doing well, played golf and has returned to work.

EXAMPLE 7—COVID-19

On Mar. 24, 2020, a 49-year-old female developed cough, dyspnoea, myalgia, pain in hip and groin, shivers but no fever. A COVID-19 test was not performed. This occurred one week after closely working together with a colleague who developed proven severe COVID-19 requiring hospital admission. Treatment with lidocaine was started 4 hours after the symptoms developed. After the initiation of continuous subdermal (superficial subcutaneous) infusion of lidocaine of 0.5 mg/kg/hr the symptoms subsided gradually and after a few hours she was practically free of symptoms. After 12 hours the lidocaine was discontinued. After a few hours the symptoms relapsed and subsided again after reinitiating the continuous subcutaneous lidocaine infusion. The lidocaine treatment lasted for 3 days.

On Apr. 1, 2020 her symptoms returned and lidocaine subdermal infusion was reinitiated. After a few days the clinical condition improved and lidocaine treatment was discontinued. The patient could work from home but experienced fatigue. After 4 weeks she recovered completely from all symptoms.

On Jul. 12, 2020, (day 1) the patient developed new symptoms comprising shivers, joint pain (knees, hips, shoulders) and conjunctivitis of the left eye. She reported sick at work. The infection probably occurred on Jul. 1, 2020. On that day she met many people during her work at the office and in the evening she went for a drink in a bar with a few colleagues. The infection occurred despite social distancing and hand sanitising. At that time no one wore a face mask. She was treated with the subdermal infusion of lidocaine (0.63 mg/kg/hr). Her symptoms improved within a few hours. On July 15 (day 4), the lidocaine infusion was stopped for several hours, she went to the GP for a COVID-19 test. On July 21 (day 10), 2020, the IgA antibody test for COVID-19 result was positive. After a week the lidocaine infusion was discontinued during daytime due to the infusion system and syringe pump being a serious obstacle for daily activity.

On day 11 the symptoms increased: Prickling sensation in the lungs, chest pain, shivers, dyspnoea, frequent yawning and dizziness. The lidocaine infusion was given 24 hours per day. The symptoms improved gradually.

On day 12 she developed increasing chest pain, shivers and pain in the proximal muscles and joints. Temperature 35.9 centigrade, $SpO_2$ (oxygen saturation) 86%, HR (heart rate) 70/min, BP (blood pressure) 110/70 mm Hg. Bronchial breath sounds were heard over the left inferior lobe of the lung and to a much lesser extent over the right inferior lobe. Subdermal lidocaine infusion (0.63 mg/kg/hr) still running and in addition she was treated with amoxicilline3×500 mg/day under suspicion of secondary bacterial pneumonia. She fell asleep and the following day all symptoms were improved significantly and the infusion was continued uninterruptedly.

On day 18 the subdermal lidocaine infusion was discontinued because the patient's daily activities were seriously hampered by the infusion system and syringe pump. A few hours later a clinical deterioration occurred with extreme fatigue, chest pain and pain in the right upper arm. The treatment was converted to transdermal lidocaine cream. Formulation: 2,5% alpha-terpineol, 20% lidocaine, 10% castor oil, 1% Polysorbate 20; 0.5% Carbopol and 56% water (lidocaine cream 200 mg/ml). As much as 400 mg cream is applied over the skin and covered by Tegaderm transparent wound dressing. But after 1 hour the symptoms did not improve and subdermal lidocaine infusion of 40 mg/hour was initiated. After 1 hour the clinical improvement was noticeable. But after 6 hours the infusion rate was increased to 63 mg/hour (1 mg/kg/hr) due to persistent symptoms. Thereafter the symptoms disappeared with the exception of the pain in the upper arm.

Day 19, the pain in the right arm remained for several weeks. The pain is mostly felt in the upper arm muscles and sometimes in the shoulder, elbow and lower arm. This led to a serious frozen shoulder syndrome.

Day 22, a period with excessive yawning and body temperature (orally measured) of 34° C.

On day 23 the patient developed undulating shivers with coughing, dyspnoea, prickling sensations of the lungs, chest pain, sore throat, headaches, yawning, conjunctivitis of the left eye and joint pain. Lidocaine infusion reduced the symptoms to tolerable levels.

On day 24 the patient has had enough of the infusion and the lidocaine infusion was converted to transdermal lidocaine cream 20% of 400 mg applied on a surface of 2×50 cm$^2$ and covered with Tegaderm. The cream was almost completely absorbed after 6 hours and each time was replaced with a new dose.

Day 25, the Tegaderm wound dressing was damaged during the night and part of the dose of the cream was lost. She woke up with sternal pain, pain in the area of the right dorsal Latissimus muscle with a feeling of malaise. SpO$_2$ 98%, HR 74/min, BP 114/71, temperature 35.3 degrees centigrade. A new cream dose was applied and an extra 100 mg cream was rubbed into the skin as a bolus dose. After 1 hour the clinical condition improved. The lidocaine 400 mg cream was set to be administered every 6 hours.

Day 26, it appeared that the cream, applied on the abdomen wall, was not absorbed well by the skin during the night. Her symptoms returned and a new dose of lidocaine cream, applied on the upper leg, reduced the symptoms within 1 hour. At 16:00 the cream was completely absorbed and the symptoms returned again. New lidocaine cream dose is effective once more.

Day 27, the resorption of the lidocaine cream applied on the arms and abdominal wall is much less than on the inner upper legs.

On day 32, 07:30, the absorption of the lidocaine cream was less than 80%. Her clinical condition was worse, the SpO$_2$ dipped regularly to 90%. Beclomethasone nose spray 2×200 g was given. She needed regular sigh and coughing to keep the SpO$_2$ above 92%. An extra 100 mg cream was rubbed into the skin as a bolus dose resulting in an improvement of the symptoms within 30 minutes. At 12:00 left knee became extremely painful and was treated again with a new cream dose and an extra 100 mg cream was rubbed into the skin as a bolus dose again resulting in the improvement of the symptoms. The total daily dose of lidocaine cream was 2000 mg.

The night of day 32 to 33 was, apart from the painful upper right arm, without any symptoms. The first night without symptoms since day 1 (Jul. 12, 2020).

On day 33 at 11:10 the patient experienced a sudden and extreme pain between her scapulae. She was dyspnoeic, she hyperventilated and her face went pale. SpO$_2$ 97%, HR 66/min, BP 112/60 mm Hg, temperature 35.3 degrees centigrade. Analysis at the hospital revealed a normal lung X-ray, normal metHb and normal d-dimer. Further routine laboratory results were also normal.

On day 35, apart from fatigue and pain in the right upper arm the patient had no other symptoms. The lidocaine cream was tapered down to 4×100 mg/d without Tegaderm covering.

Day 46, 03:30, SpO$_2$ alarm at 86%, HR 55/min, BP 115/70 mm Hg, prickling sensations of the lung, left conjunctivitis. The lidocaine cream was removed and continuous subdermal infusion of 0.63 mg/kg/hr lidocaine was initiated. The symptoms improved within 30 minutes. The painful right upper arm remained unchanged.

After 1 week the lidocaine infusion was discontinued.

On day 61 at 04:20 a new episode with prickling sensations of the lung, left conjunctivitis and increased painful upper right arm developed. Continuous subdermal infusion of 0.63 mg/kg/hr lidocaine was initiated and the symptoms subsided. Lidocaine infusion was discontinued after 8 hours. At 19:40 after dinner, the patient developed shivers, was feeling unwell and had to go to bed. Temperature 34.1, BP 96/60 mm Hg, SpO$_2$ 100%, HR 86/min. Continuous subdermal infusion of 0.63 mg/kg/hr lidocaine was re-initiated with 400 g of beclomethasone nose spray and oral hydrocortisone. The symptoms quickly subsided.

On day 66 she felt good apart from the painful right upper arm. The pain in the upper arm is fluctuating in intensity and sometimes migrates to the shoulder or elbow. The general practitioner was not convinced that this had anything to do with COVID-19. The lidocaine infusion was discontinued.

On day 67, she made a trip by car, as a passenger, to visit friends in a place 200 km from home.

Day 85, after almost 3 weeks with no symptoms other than a fluctuating pain in the upper arm, the prickling sensations of the lung returned. SpO$_2$ 96%, HR 90/min, BP 95/68 mm Hg, temperature 33.5 degrees centigrade. Sublingual lidocaine 3×100 mg/d was initiated. The lidocaine was kept in the mouth for 15 minutes and then swallowed. Inhalation of the lidocaine solution was avoided. Formulation of the lidocaine: Xylocaine 5 g in 50 ml (10% solution, 100 mg/ml), ethanol 96%, polyethylene glycol 400, banana essence, and purified water.

From day 85 on, after the initiation of the sublingual lidocaine treatment, the patient experienced prickling sensations and oppressive feeling on her chest in the morning before she took the medication and at the end of the day before taking the sublingual lidocaine. These symptoms disappeared 20 minutes after the administration of sublingual lidocaine. This occurred repeatedly almost every day.

EXAMPLE 8—COVID-19

On Dec. 20, 2020, a 46-year-old male developed a runny nose, mild headache, stiffness and severe pain of the neck and right shoulder, loss of smell and strongly diminished taste. He felt washed-out and lethargic. The patient had had contact with a COVID-19 patient 5 days earlier. On day 2 after the initiation of the symptoms the PCR swab test for COVID-19 was positive. The following days symptoms were progressive.

On day 5 the patient received 5×60 mg lidocaine using a metered dose. The drug was administered sublingually and kept in the mouth for 15 minutes. Thereafter, the lidocaine solution was swallowed.

Inhalation of the lidocaine was avoided. Formulation of the lidocaine: Xylocaine 5 g in 50 ml (10% solution, 100 mg/ml), ethanol 96%, polyethylene glycol 400, banana essence, and purified water. On day 6 (24 hours after the initiation of the treatment) the runny nose, headache, neck pain and neck stiffness disappeared.

On day 6 the patient received lidocaine 4×60 mg/d and from day 7 on the patient was treated with lidocaine 3×60 mg/d. On day 9 the patient is much less lethargic, felt to have more energy and started cleaning his house thoroughly. He reported dry mouth feelings for the first time. On day 8 all symptoms, with the exception of dry mouth feelings and mild fatigue, disappeared completely. On day 11 the patient took a 1 hour walk and felt good.

EXAMPLE 9—ARDS by *Staphylococcus* Sepsis

An example in off-label use of lidocaine as the ultimate drug (*ultimum* remedium) to treat a patient suffering from severe ARDS. A 43-year-old female was admitted to an ICU in the Hague region at the end of 2019. She developed severe ARDS from *staphylococcus* sepsis. This sepsis developed after intravenous administration of contrast fluid for an MRI image. The patient was put on mechanical ventilation. Despite adequate antibiotic treatment, the ARDS and sepsis deteriorated further leading to insufficient oxygenation under mechanical ventilation with haemodynamic instability requiring very high doses of nor-adrenaline and vasopressin. She was connected to ECMO (extracorporeal membrane oxygenation) and transferred to the University Hospital Rotterdam. It was planned to keep the patient on the ECMO, operatively remove the lungs and to treat the patient with antibiotics for 2 months to clear the thorax cavities from microbes. This procedure would then be followed by a lung transplantation. The haemodynamic instability and the poor oxygenation, even with ECMO therapy, motivated the intensivist in charge to treat the patient with continuous low dose lidocaine aiming at the inhibition of the $P2X_7R$. Within 1.5 hours after the initiation of the continuous lidocaine infusion of 1 mg/kg/hour, the patient's condition stabilised. Over the following days the noradrenalin and vasopressin medication could be tapered down and after several days the ECMO was disconnected because oxygenation with regular ventilation was restored. Needless to say that the planned lung transplantation was cancelled. After 1.5 months, the patient was weaned from the ventilator and was transferred to the ward. The patient received lidocaine for a period of 2 weeks.

EXAMPLE 10—Polymyalgia rheumatica

In January 2012 a 59-year-old man suffered from progressive muscle pains, initially referred to as statin related. Could hardly turn over in bed. The patient experienced varying loss of strength, weight remained stable 54 kg. No fever. In addition, the patient reported fatigue and general malaise. No familial skin or muscle disorders, but asthma and CVD. Eighteen months previously, the patient had a tick bite and developed erythema with erythema chronicum migrans (ECM). On the suspicion of an infection with *Borrelia Burgdorferi* the patient was treated with amoxicillin for 4 weeks. Laboratory results revealed an increasing erythrocyte sedimentation rate of 47 mm/hr (Nov. 1, 2012) and 85 mm/hr (February 2013). Chest X-ray and CT scan of the chest and abdomen were unremarkable. The diagnosis was polymyalgia rheumatica. The patient was initially treated with high dose corticosteroids. This medication was tapered down and discontinued after 6 months.

In September 2019 the symptoms recurred. The patient was initially treated with nocturnal continuous subdermal lidocaine infusion of 0.5 mg/kg/hr for 8 hours with a frequency of 2 x/week. The symptoms disappeared after the first treatment. After a few months the lidocaine subdermal infusion was replaced with transdermal 5% lidocaine ointment 300 mg twice a day. This therapy was ineffective. On Sep. 10, 2020 the patient started to use sublingual lidocaine 2×60 mg/d. The lidocaine was kept in the mouth for 15 minutes and then swallowed. Inhalation of the lidocaine solution was avoided. Formulation of the lidocaine: Xylocaine 5 g in 50 ml (10% solution, 100 mg/ml), ethanol 96%, polyethylene glycol 400, banana essence, and purified water. The symptoms disappeared within 1 hour and (during treatment) did not return until the end of the follow-up on Jan. 2, 2021.

EXAMPLE 11—Psoriatic Arthritis

A 60-year-old female was presented with cutaneous herpes zoster infection of her back extending to the abdomen wall. Four years earlier she developed psoriasis. In the previous year she developed progressive rheumatoid arthritis and lichen planus. The symptoms were progressive and since a few weeks she was not able to cook her meals. She could barely get dressed and get undressed. She had been treated with corticosteroids and methotrexate. In the beginning of July 2020 a very painful herpes zoster infection of the trunk emerged and the patient was treated with morphine. Morphine did not subside the pain but she developed obstipation. This is the situation when she was presented to us. On Aug. 8, 2020 she started with our treatment consisting of lidocaine cream 10%. Formulation: 2,5% alpha-terpineol, 10% lidocaine, 10% castor oil, 1% Polysorbate 20; 0.5% Carbopol and 66% water (lidocaine cream 100 mg/ml). Lidocaine cream dosage was 2×200 mg/day applied over the skin of her forearm and covered by Tegaderm transparent wound dressing. Every day, the location of the applied cream was alternately on the left and right forearm. The morphine treatment was tapered down. Because the Tegaderm covering damages the skin she changed to cling film covering wrapped with elastic bandage.

The obstipation disappeared within 2 days, the herpes zoster infection was rapidly declining and after 14 days her sense of well-being increased from 3 to 7.5 on a scale of 10. She could perform her daily activities at home normally. After 4 weeks she could easily do some gardening and her capacity to perform her daily activities returned to normal.

EXAMPLE 12—Spondylarthritis

A 62-year-old patient from Italy was presented with an intractable progressive and debilitating degenerative disease of the vertebrae (L2-L3, L3-L4 and L4-L5). He suffered severe pain, could hardly walk, could no longer do his work as a crane operator and was no longer able to practice his hobby (repairing racing motorcycles). The symptoms had been progressive for 20 years. Pain killers had no effect.

In December 2019, the patient received 2×1400 mg/d lidocaine patches. To prevent skin irritations, the patches were administered on alternate locations on the skin. According to the patient, 70% and 90% of the symptoms have disappeared after 4 days and 2 weeks, respectively. He has little pain, went back to work and was able to pick up his hobby again.

EXAMPLE 13—Chronic Interstitial Cystitis (Chronic Inflammatory Bladder Condition)

An 88-year female, co-morbidity hypertension, glaucoma, diabetes type II with renal dysfunction, chronic inflammation of the uterus and the bladder. The past 2 years she complained about intractable progressive extreme pain of the bladder especially during micturition. Oxycodone (morphine analogue), paracetamol and antibiotic treatment had no effect on her symptoms. Treatment with continuous subcutaneous lidocaine of 1 mg/kg/hr reduced her symptoms gradually and after 2 days she was practically free of symptoms. After 1 week the treatment was discontinued due to problems with the supply of the drug and her symptoms reoccurred. After restarting the lidocaine infusion her symptoms disappeared once again.

EXAMPLE 14—Knee Arthrosis

A 43-year-old female suffered from gonarthrosis (knee osteoarthritis) of the right knee. There is hydrops of the right knee and is extremely painful. Her maximal walking range is 100 m before the pain forced her to stop walking and to sit down. She could barely climb the stairs at home and she was not able to ride her bicycle. MRI showed hydrops in the right knee joint. Because there is a defect in the ventral part of the femorotibial cartilage tissue revealed by MRI she was rejected for a knee extraction therapy. On Jan. 25, 2020, she received treatment with 2×1400 mg/d lidocaine patches. Within 6 weeks the hydrops of the right knee and the pain improved, her walking range was extended to >500 m, she could climb the stairs and after 8 weeks she could ride her bicycle.

EXAMPLE 15—Multiple Sclerosis

A 46-year-old patient was diagnosed with relapsing-remitting multiple sclerosis (RRMS) in 2005. In 2005-2006 she was treated with Avonex. In January 2020 she was presented with fatigue. She had to take a rest between 10: AM and 14:00 because of fatigue. Her neurological symptoms consist of paraesthesia of the right arm. We treated her with 1×700 mg/48 hours lidocaine patches. After 4 weeks her fatigue improved, she could skip resting during the days and she felt to have more energy for her daily activities.

EXAMPLE 16—Advanced Cervix Carcinoma and Renal Dysfunction

A 65-year-old female was diagnosed with advanced cervix carcinoma in July 2018. The tumour mass blocked both ureters and caused bilateral hydronephrosis. The hydronephrosis was drained successfully and the patient was treated with paclitaxel and bevacizumab. *In* October 2018 renal function impairment developed. In August 2019 the CT scan of the chest and abdomen revealed a large tumour mass in the pelvis cavity, multiple para-iliac lymph node metastasis and a mass surrounding the pancreas. She developed cancer-related ascites. The conclusion was that the tumour growth was progressive. But because of the progressive impairment of the renal function, the intended therapy with carboplatin and gemcitabine was postponed.

On Sep. 15, 2019 the patient started to receive continuous subdermal lidocaine infusion of 1 mg/kg/hr. The renal function improved. After 6 weeks the renal function improvement was such that the patient could be treated with carboplatin and gemcitabine. Five months later, in February 2020, the tumour growth was stabilised and the chemotherapy treatment could be discontinued. At that time she was still on lidocaine infusion.

EXAMPLE 17—Diverse Cancer 10 patients: Prostate cancer (2 patients), exocrine pancreatic cancer (4 patients), colon cancer (2 patients), cervical carcinoma (1 patient) and breast cancer (1 patient). All patients had no more options for further cancer treatment left and all patients were treated with palliative opiates. We prescribed the patients continuous subcutaneous lidocaine 1 mg/kg/hr instead of morphine.

In 7 patients the relieve of pain, nausea, and/or extreme fatigue was achieved within 2 hours and in the remaining patients within 48 hours. This improved further in the following week and stabilised for weeks.

For example, an 81-year-old patient with a terminal metastatic colon cancer with much pain, discomfort and malignant ascites, improved so much that after 3 weeks he could perform with his rock band in a wheel chair.

Sickness impact profile for disability (SIP68) was applied for inventory data. Before treatment: SIP68: 48 (range 18-68). After 3 days: SIP68: 33 (range 12-58), all patients were improved. After 7 days: SIP68: 28 (range 12-56), all patients were improved.

EXAMPLE 18—Amyotrophic Lateral Sclerosis (ALS)

A 63-year-old male was referred to the outpatient clinic for the analysis of muscle cramping in both calves, a left foot drop and weakness in both hands, shoulders and legs. Muscle cramping occurred almost exclusively after volitional movement. No memory deficit and no familial history of a disease were noted.

On physical examination atrophy of bilateral m. infraspinatus, m. supraspinatus, thenar and hypothenar eminences and left calf. There were hyperreflexia of the lower limb and bilateral extensor response of the hallux (positive Babinski sign). Muscle fibrillation was seen over the calves and shoulders. Muscle strength physical examination score according to MRC scale (Medical Research Council, UK, mrc.ukri.org): Upper arm abduction left 4, right 4; Upper arm adduction left 5, right 5; Elbow flexion left 4, right 4; Elbow extension left 5, right 5; Knee flexion left 4 right 4; Knee extension left 5, right 5; Foot extension left 1, right 1; Foot flexion left 2, right 2; The remaining muscles were not affected.

Imaging (CT scan and MRI scan) of the spine ruled out any structural impinging of the motor nerve tracts. EMG revealed denervation in the limb muscles. The diagnosis was ALS.

The patient was treated with sublingual lipophilic lidocaine base 4×100 mg/d (Xylocaine spray 5 g in 50 ml in a metered spray bottle). The patient kept the lidocaine solution in the mouth for 15 minutes, then the patient swallowed the solution as intended.

After one week the patient noted that the muscle cramping had gradually disappeared. After 3 weeks his muscle strength started to improve gradually. Six months after the initiation of lidocaine therapy a repeat muscle strength examination (using MRC scale) revealed: Upper arm abduction left 5, right 5 (improved); Elbow flexion left 4, right 4 (unchanged); Knee flexion left 5, right 5 (improved); Foot extension left 2, right 2 (improved); Foot flexion left 3, right 3 (improved); The remaining muscles were not affected. The treatment resulted in clinically significant improvement of the symptoms of the disease.

EXAMPLE 19—Alzheimer's Dementia

A 72-year-old male had increasingly developed loss of memory. The symptoms started 6 years earlier with episodic loss of memory gradually followed by the inability to remember new information. In contrast old memories seemed to be intact. The symptoms developed to such an extent that social functioning, daily activity as cooking, gardening and shopping were severely affected. No familial history of cardiovascular, psychiatric or neurological diseases was present.

Physical examination revealed no abnormalities. The Mini Mental State Examination (MMSE) Test total score was 15 (severe cognitive impairment). Routine blood chemistry and haematology were normal. Analysis of the thyroid function, blood rheumatology screening vitamin B12 and homocysteine showed no abnormalities. Urine (24-hour sample) analysis showed no evidence of heavy metal poisoning. Routine Chest X-ray was normal. MRI of the brain was unremarkable. The diagnosis was Alzheimer's disease.

Lumbar puncture revealed decreased levels of β-amyloid (Aβ42).

The patient was transferred to a dementia nursing home. The patient received sublingual lipophilic lidocaine base 4×100 mg/d (Xylocaine spray 5 g in 50 ml in a metered spray bottle). The patient kept the lidocaine solution in the mouth for maximal 15 minutes, then swallowed the solution as intended. Medication compliance was secured by a specialised nurse.

Gradually the memory imprinting capacities increased and after 3 months the MMSE Test total score was 23 (mild cognitive impairment). The treatment resulted in clinically significant improvement of the symptoms of the disease.

EXAMPLE 20—Idiopathic Parkinson's Disease

A 76-year-old male suffered from a progressive tendency to fall (postural instability). The symptoms started 8 years before the patient was referred to the clinic. In addition, 3 years later he developed progressive trembling of the right arm especially when the arm is not moving (rest tremor). Rest tremor of the left arm developed 2 years after the onset of the right arm tremor.

The patient was treated with levodopa and initially the symptoms improved clearly. After 6 years the symptoms returned and after increasing the levodopa dosage the patient developed levodopa-induced chorea. The patient had never been treated with neuroleptic drugs.

There was no history of repeated strokes, repeated head injury, encephalitis, oculogyric crises, supranuclear gaze palsy, loss of memory autonomic symptoms or MPTP ((1-methyl-4-phenyl-1,2,3,6-tetrahydropyridine) abuse. Cerebral MRI was unremarkable. The diagnosis was idiopathic Parkinson's disease.

The patient was treated with sublingual lipophilic lidocaine base 4×100 mg/d (Xylocaine spray 5 g in 50 ml in a metered spray bottle). The patient kept the lidocaine solution in the mouth for maximal 15 minutes, then the patient swallowed the solution as intended.

After 1 month the patient reported that the tendency to fall has gradually improved. The tremor had almost disappeared. The treatment resulted in clinically significant improvement of the symptoms of the disease.

EXAMPLE 21—Epileptic Seizures

A 30-year-old female was transferred to an emergency room after a car collision. She was sitting beside the driver. She complained of headache. Her medical history was clean.

On physical examination the Glasgow Coma Score (GCS) was 15 of 15 at admission. A subcutaneous hematoma was observed on her forehead. No other abnormalities were found.

CT scan of the head and cervical spine was unremarkable. One hour after arrival her level of consciousness started to decrease and she developed generalised epileptic seizures.

Treatment with repeated 10 mg of intravenous diazepam had no effect and the patient was intubated and deeply sedated with continuous midazolam infusion. A repeat CT scan 4 hours after arrival at the emergency room showed a haemorrhagic contusion lesion in the left parietal lobe. The patient was admitted to the ICU, put on mechanical ventilation and was put into a pentobarbital coma under EEG monitoring. After 5 days the patient was weaned from pentobarbital and generalised epileptic seizures started to develop in increasing intensity. The diagnosis was posttraumatic epileptic seizures.

Treatment with subdermal (superficial subcutaneous) lidocaine HCL (20 mg/ml solution) of 1 mg/kg/hour was initiated and within 30 minutes the seizures disappeared. EEG showed that epileptic activity of the brain had disappeared. Eight hours later the patient regained consciousness and after 4 hours she was weaned from mechanical ventilator and was extubated.

The following day, the GCS was 15 of 15 and on physical examination no neurological deficits were found. The patient remained on continuous subdermal lidocaine treatment for 2 weeks. The treatment resulted in clinically significant improvement of the posttraumatic epileptic seizures.

EXAMPLE 22—Multiple Sclerosis

A 56-year-old female was diagnosed with primary progressive multiple sclerosis (PPMS) 10-years earlier. The diagnosis was confirmed with a cerebrospinal MRI and CSF findings.

Treatment with ocrelizumab and dexamethasone did not improve the symptoms.

At the time that she was referred to us, the score on the Kurtzke expanded disability status scale EDSS was 7.5 (Kurtzke (1983) *Neurology.* 33 (11): 1444-52). The patient was restricted to a wheelchair and was unable to walk more than a few steps.

We treated the patient with sublingual lipophilic lidocaine base 4×100 mg/d (Xylocaine spray 5 g in 50 ml in a metered spray bottle). The patient kept the lidocaine solution in the mouth for maximal 15 minutes, then the patient swallowed the solution as intended.

In the following weeks her clinical condition improved. After 3 months the EDSS was improved from 7.5 to 5.5, she could walk without an aid for about 120 meters but she still needed an aid to fulfil her full daily activity. The treatment resulted in clinically significant improvement of the EDSS score after treatment with sublingual lidocaine.

EXAMPLE 23—Diabetic Polyneuropathy

A 72-year-old female with diabetes mellitus was diagnosed with diabetic polyneuropathy. She suffered from symmetric tingling feelings in her hands and feet and loss of muscle strength in her hands. Medication: intermediate-acting insulin 2×12 U/d and 3×500 mg/d metformin.

Physical examination revealed paraesthesia and loss of sensibility over her hands and feet and loss of muscle strength (MRC 4 of 5) in both finger flexors and extensor muscles of the hand. The patient was treated with sublingual lipophilic lidocaine base 4×100 mg/d (Xylocaine spray 5 g in 50 ml in a metered spray bottle). The patient kept the lidocaine solution in the mouth for maximal 15 minutes, then the patient swallowed the solution as intended.

After a few days the tingling feelings in her hands and feet disappeared completely and after 3 months the muscle strength of her hands was improved significantly. The treatment resulted in clinically significant improvement of the diabetic polyneuropathy.

EXAMPLE 24—Myasthenia Gravis

A 36-year-old male was diagnosed having myasthenia gravis. He suffered from muscle weakness of the arms and hand after physical activity. The diagnosis was confirmed with EMG and positive test for antibodies against acetylcholine receptor (AChR). He was treated with oral anticholinesterase drug (mestinon) 4×60 mg/d. During an infection with influenza A virus, the patient developed severe weakness of his arms and hands and the anticholinesterase treatment was no longer effective. The patient was treated with sublingual lipophilic lidocaine base 4×100 mg/d (Xylocaine spray 5 g in 50 ml in a metered spray bottle). The patient kept the lidocaine solution in the mouth for maximal 15 minutes, then the patient swallowed the solution as intended. Within 4 hours the muscle weakness of the arms and hand improved significantly. In addition, the influenza A viral infection symptoms disappeared almost completely. The treatment was continued for 2 weeks. The treatment resulted in clinically significant improvement of the muscle weakness in exacerbation of myasthenia gravis symptoms.

EXAMPLE 25—Chronic Obstructive Pulmonary Disease (COPD)

A 67-year-old female was diagnosed with COPD. The diagnosis was confirmed by the finding of an $FEV_1$ of 72% (moderate COPD) during spirometer testing. Chest X-ray and routine blood tests are unremarkable. The patient was treated with beclomethasone 2×40 microgram/d. The following 6 years she suffered from progressive shortness of breath during physical exercise such as climbing a staircase at home and cycling. Her daily activities were severely affected by her symptoms. The $FEV_1$ decrease to 60%. The patient was treated with sublingual lipophilic lidocaine base 4×100 mg/d (Xylocaine spray 5 g in 50 ml in a metered spray bottle). The patient kept the lidocaine solution in the mouth for maximal 15 minutes, then the patient swallowed the solution as intended. Within a week she was improved and could climb the staircase and ride her bicycle without developing shortness of breath. After 3 months a repeat spirometer test showed that her $FEV_1$ was improved to 84% (mild COPD). Lidocaine treatment relieved her COPD symptoms.

EXAMPLE 26—Graves' Disease

A 50-year-old female had been diagnosed with Graves' disease for a few years. The hyperthyroidism had been treated and was under control, but the eye symptoms were still clearly present. Until a year ago, she was given five steroid infusions, which showed only short-term improvement in the eyes. The last treatment proposal was to perform a double-sided surgical decompression of the orbits. Due to diplopia as a possible side effect, the patient had not yet consented to this operation. The eye status prior to lidocaine cream application to the eyelids was as follows for both eyes: redness of the conjunctiva; a moderate non-fluid peri-orbital swelling; absence of eyelid erythema; no signs or symptoms of optic neuropathy or corneal exposure. Three times daily eyelid application of a Xylocaine ointment 5% resulted in a significant improvement of the redness of the conjunctiva and the periorbital swelling. The treatment resulted in clinically significant improvement of the symptoms of the disease.

EXAMPLE 27—Ulcerative Colitis

A 40-year-old female was diagnosed ulcerative colitis 5 years ago. He symptoms were episodes of abdominal pain, bloody diarrhoea with mucus, anaemia and weight loss. With the exception of anaemia, routine blood laboratory test was unremarkable. CT scan showed mural thickening of about 8 mm in several segments of the colon. Colonoscopy revealed segmental colonic inflammation with erythema, loss of normal vascular pattern, granularity, erosions, bleeding, and ulcerations. There is a clear distinct demarcation between inflamed and normal bowel mucosa. No signs of dysplasia or malignant conversion were observed. Histopathology showed decreased crypt density, irregular aspect of the mucosa and diffuse inflammation. No granulomas were found. In the previous episodes of exacerbation of the colitis, the patient responded well to treatment with oral mesalamine CR of 3×400 mg/d. But in this episode of exacerbation the symptoms did not respond to mesalamine treatment. The patient was treated with sublingual lipophilic lidocaine base 4×100 mg/d (Xylocaine spray 5 g in 50 ml in a metered spray bottle). The patient kept the lidocaine solution in the mouth for maximal 15 minutes, then the patient swallowed the solution as intended. The symptoms gradually decreased in 48 hours and completely disappeared after 3 days. Sublingual lidocaine was continued for 2 weeks and the following months the patient remained symptom free. Lidocaine eradicated the symptoms of the disease.

EXAMPLE 28—Inflammatory Bowel Disease

A 1.5-year-old dog developed small holes in the perianal region, white opaque fluid oozing from the opening of the holes. The size of the holes became progressively larger and the fistulae started to smell badly and he started to develop diarrhoea. The dog was in pain especially during defecation. Physical examination revealed very painful and inflamed perianal fistulae. The dog was diagnosed with inflammatory bowel disease with perianal fistulae. The diagnosis was inflammatory bowel disease with perianal fistulae. A veterinarian decided to operate and remove the anal sacs. After the operation the disease showed an accelerated progress and the suffering increased significantly. The dog was treated with lipophilic lidocaine base 4×100 mg/d (Xylocaine spray 5 g in 50 ml in a metered spray bottle) applied into the largest fistula. After 1 week the oozing opaque fluid secretion and the bad odour had disappeared. Even during defecation the pain was significantly alleviated. The lining of the fistula started to produce granulation tissue. Lidocaine alleviated the symptoms and infection of anal fistulae.

EXAMPLE 29—Allergic Reaction to Processionary Caterpillar Toxin

A 33-year-old male accidentally drove over oak processionary caterpillars. He immediately developed a pruritic rash on the arms, chest, face and neck. A few minutes later he was dyspnoeic and had difficulties with breathing. We treated the patient with sublingual lidocaine base 100 mg (Xylocaine spray 5 g in 50 ml in a metered spray bottle). The patient kept the lidocaine solution in the mouth for maximal 15 minutes, then the patient swallowed the solution as intended. Within 10 minutes the symptoms started to improve. After 15 minutes all respiratory symptoms had disappeared and after 1 hour the itching skin rash was improved dramatically. The treatment was discontinued after 48 hours (4×100 mg/d) and the symptoms did not return. The treatment resulted in clinically significant improvement of allergic response to processionary caterpillar toxin.

EXAMPLE 30—Rheumatoid Arthritis

A 62-year-old female was diagnosed with rheumatoid arthritis of bilateral joints of herwrists and fingers. She suffered from severely painful, swollen and warm joints. Her capacity to fulfil the daily activities were severely disrupted and she was almost fully dependent on others. Blood tests for rheumatoid factor (RF) and anti-citrullinated protein antibodies (ACPAs) were clearly positive. The clinical disease activity index score for rheumatoid arthritis (Aletaha & Smolen, Clin. Exp. Rheumatol. 2005 September-October; 23 (5 Suppl. 39):S100-8) was 52 points of a total of 76 points indicating a high disease activity. The diagnosis was rheumatoid arthritis.

Treatment with disease-modifying antirheumatic drugs (DMARDs) such as methotrexate and tocilizumab did not improve the symptoms and the patient suffered from side effects. the patient was treated with sublingual lipophilic lidocaine base 4×100 mg/d (Xylocaine spray 5 g in 50 ml in a metered spray bottle). The patient kept the lidocaine solution in the mouth for maximal 15 minutes, then the patient swallowed the solution as intended.

After 4 weeks the inflamed joints of her wrist and hands had almost disappeared. She still complained of stiffness in these joints. The clinical disease activity index score for rheumatoid arthritis was improved from 52 points of a total of 76 points to 2 points indicating a remission. The treatment resulted in clinically significant improvement of the clinical disease activity after treatment with sublingual lidocaine in severe rheumatoid arthritis.

EXAMPLE 31—Ischaemic Cardiomyopathy in a Patient with Diabetes Mellitus

A 61-year-old male with a 15-year history of diabetes mellitus. Eight years earlier he underwent a stenting procedure followed by a coronary artery bypass graft (CABG) operation because of a three-vessel disease. The last 5 years the patient suffered from repeated chest pain, a gradually increasing dyspnoea at night and during exercise and extreme fatigue. His blood pressure was 140/90 mm Hg. He was diagnosed with ischaemic cardiomyopathy. The estimated transthoracic echocardiographic cardiac ejection fraction was 31%. The diagnosis was ischaemic cardiomyopathy. The patient was not eligible for surgical treatment and requested us to treat him with lidocaine. We treated the patient with sublingual lipophilic lidocaine base 4×100 mg/d (Xylocaine spray 5 g in 50 ml in a metered spray bottle). The patient kept the lidocaine solution in the mouth for maximal 15 minutes, then the patient swallowed the solution as intended. After 3 weeks the patient reported that the chest pain episodes were significantly diminished, the dyspnoea was clearly improved and he felt he had more energy during the day. After 3 months a repeat transthoracic echocardiographic showed that the cardiac ejection fraction was improved from 31% to 42%. The treatment resulted in clinically significant improvement of the symptoms and cardiac function in a patient with severe ischaemic cardiomyopathy.

EXAMPLE 32—Acute Lumbago in a Patient with a History of Polymyalgia Rheumatica

A 67-year-old man with a history of polymyalgia rheumatica suffered from severe backpain. The previous day he has been cycling over a 45 km distance with a road bike equipped with a drop handlebar. The ride was tough due to a strong headwind during most of the trip.

The following morning he woke up with severe lower backpain. The lumbago restricted him to straighten his back. He could cautiously walk with an extreme bent posture and could hardly climb the stairs. The patient was treated with sublingual lipophilic lidocaine base 4×100 mg/d (Xylocaine spray 5 g in 50 ml in a metered spray bottle). The patient kept the lidocaine solution in the mouth for 15 minutes, then the patient swallowed the solution as intended. After 30 minutes 95% of the symptoms disappeared. The patient could resume a normal upright posture and had no difficulties in walking and climbing the staircase.

EXAMPLE 33—Systemic Lupus Erythematosus (SLE)

A 79-year-old man with confirmed SLE was referred to the hospital. The diagnosis SLE was established when the patient was 42 years old. In the course of time he was regularly admitted to the hospital because of recurrent SLE-induced pericarditis with pericardial effusion, peritonitis and pleuritis. A few days before he was referred to us a new episode of peritonitis started to develop. He suffered from abdominal pain, nausea and an obvious abdominal distension due to ascites. The patient had a feeling of having lack of energy. Laboratory examination of the peritoneal fluid: IL-6 11.000 µg/ml (while serum IL-6 was 28 µg/ml) and LDH 102 IU/L. The patient was treated with sublingual lipophilic lidocaine base 4×100 mg/d (Xylocaine spray 5 g in 50 ml in a metered spray bottle). The patient kept the lidocaine solution in the mouth for 15 minutes, then the patient swallowed the solution as intended. The clinical symptoms disappeared in the course of 6 days and after 2 weeks the abdominal distension disappeared completely. The treatment with sublingual lidocaine was continued.

Section A: P2X7R antagonists
  A. Monoclonal antibodies specific against P2X7R
  B. Chemical compounds
    a. Amides derivatives
      i. Oxo-proline amide derivatives as described in KR101398264B1
      ii. Amino amide group: Lidocaine, Articaine, Bupivacaine, Cinchocaine (Dibucaine), Etidocaine, Levobupivacaine, Lidocaine (Lignocaine), Mepivacaine, Prilocaine, Ropivacaine, Trimecaine
    b. Amino ester derivatives
      i. Procaine, Benzocaine, Chloroprocaine, Cocaine, Cyclomethycaine, Dimethocaine (Larocaine), Piperocaine, Propoxycaine, Proparacaine, Tetracaine (Amethocaine)
    c. Phenyl-Substituted 5,6-Dihydro-[1,2,4]triazolo[4,3-a]pyrazine P2X7 Antagonists
    d. Bicycloheteroaryl compounds as p2x7 modulators and uses thereof (WO2007/109192)
  C. P2X7R inhibitors used in clinical trials and tested in humans
    a. CE-224,535 500 (Pfizer),
    b. AZD9056 (Astra-Zeneca)
    c. JNJ-54175446 (Johnson and Johnson).
    a. P2X7R inhibitors published by Mehta N, et al. *Bioorg Med Chem*, 201422 (1) 54-88 Existing P2XR inhibitors not selective for P2X7R only: PPADS tetrasodium salt, brilliant blue G (BBG), oxidised ATP (o-ATP)
    b. Existing specific 2X7R inhibitors: KN-62, AZ9056, A-740003, A-438079, GSK314181A, A-804598, A-839977 and AZ-116453743.
    c. Parent scaffold-based classification, 181 compounds: Adamantane amide derivatives, Triazole derivatives, Diarylimidazolidine derivatives, Pyroglutamic acid amide derivatives, Pyrazole acetamide derivatives, Dihydrodibenzo [a,g]quinolizinium derivatives, Tetrazole derivatives, Tyrosine based derivatives, Pyrazolodiazepine derivatives, Imidazoles derivatives, Benzamides derivatives, KN62 analogs derivatives, Natural antagonists of P2X7R.
d. Three P2X7R inhibitors from natural product extracts: Massadine, Stylissadine A and Stylissadine B.
a. P2X7R inhibitors published by Caseley E A, et al. *Biochem Pharmacol* 2016 (116) 130-13973 top-ranked compounds after virtual screening of approximately100,000 structurally diverse compounds against the ATP-binding pocket in the hP2X7R: C1 until C73.
b. Three of these compounds appeared to effectively inhibit transmembrane currents due to P2X7R activation and macropore forming (YO-PRO-1 uptake): C23, C40 and C60. P2X7R inhibitors published by Bin Dayel A, et al. *Mol Pharmacol* 2019, 96 (3) 355-363 AZ11645373, brilliant blue G, KN-62, calmidazolium and ZINC58368839.
a. P2X7R inhibitors published by North R A, et al. *Physiol Rev* 2002, 82, (4), 1013-67 Existing P2XR inhibitors not selective for P2X7R only: BBG, PPADS, suramin, o-ATP.
b. Existing specific 2X7R inhibitors: A-438079, A-804598, A-740003.0, KN-62, AZ10606120, AZ11645373, GW791343 and JNJ47965567
d. P2X7R inhibitors published by Sluyter, *Adv Exp Med Biol—Prot Rev* 2017, (19)—17-53 Existing P2XR inhibitors not selective for P2X7R only: BBG, o-ATP, PPNDS, PPADS, MRS2159, NF279, NF449.
e. Existing specific 2X7R inhibitors: AACBA, AstraZeneca, A-438079, A-804598, A-740003.0 and KN-62.
D. P2X7R inhibitors published by Carroll, et al. *Purinergic signal* 2009, 5, (1) 63-73 57 Compounds: Adamantane carboxamides, Aryl carbohydrazides, Cyanoguanidines, Aryltetrazoles/aryltriazoles
E. P2X7R inhibitor published by Donnelly-Roberts D L, et al., *Neuropharmacology* 2009, 56, (1), 223-9. [3H] A-804598 ([3H]2-cyano-1-[(1S)-1-phenylethyl]-3-quinolin-5-ylguanidine)
F. P2X7R inhibitor published by Ruiz-Ruiz q, et al., *Front Mol Neurosci* 2020, 13, 93. AZ11645373, AZD-9056, A-438079, A740003, CE-224,535, GSK-1482160, JNJ-47965567, A-804598, 2, JNJ-54175446, JNJ-55308942

Section B: Diseases involving hyperinflammation—involving the activation of P2X7R of the immune system
1. Autoimmune diseases and immune-related diseases
2. Treatment-induced immune-related diseases
3. Infectious diseases
4. Cardiovascular diseases and neurovascular diseases
5. Neuroinflammatory and neurodegenerative diseases
6. Epileptic disorders
7. Affective disorders and psychiatric syndromes
8. Fibrosis
9. Cancer-related disorders
10. Cancer and neoplasms
11. Trauma and posttraumatic syndromes
12. Post-organ transplantation syndromes including transplanted organ rejection.

1. Autoimmune Diseases and Immune-Related Diseases
Primary Immunodeficiency
Systemic Inflammatory Diseases:
(1) Systemic syndrome in advance cancers (SIRS), (2) Sepsis: a. Bacterial sepsis: *Pseudomonas* spp., *Staphylococcus* spp., *Streptococcus* spp., b. Viral sepsis and ARDS: Influenza A virus, SARS, MERS, COVID-19, etc., c. Overwhelming post-splenectomy sepsis: *Streptococcus pneumoniae, Haemophilus influenzae, Neisseria meningitidis*, d. Babesiosis: *Babesia microti* (U.S.), *B. divergens* (Europe), e. Meningococcemia with sepsis and meningitis: *N. meningitides*, f. Rocky Mountain spotted fever (RMSF): *Rickettsia rickettsia*, g. Purpura fulminans: *S. pneumoniae, H. influenzae, N. Meningitidis*, h.
Erythroderma, toxic shock syndrome: Group A *Streptococcus, Staphylococcus aureus*, i. Necrotizing fasciitis: Group A *Streptococcus*, mixed aerobic/anaerobic flora, Community-Associated Methicillin-Resistant *Staphylococcus Aureus* (CA-MRSA),j. Clostridial myonecrosis: *Clostridium perfringens*, k. Gas gangrene, (3) Hyperinflammation and cytokine storm, (4) Anaphylactic reaction including shock, (5) Systemic allergic reactions, (6) Systemic reactions (SIRS) following trauma, (7) Acute post-operative (post-transplantation) inflammation and SIRS.
Endocrine diseases:
(1) Type I and type II diabetes (2) Addison's disease (3) Autoimmune polyendocrine syndrome (APS) type 1, 2 and 3 (4) Autoimmune pancreatitis (AIP), (5) Autoimmune thyroiditis (6) Ord's thyroiditis (7) Grave's disease, (8) Hashimoto's disease, (9) Autoimmune oophoritis, (10) Endometriosis (11) Autoimmune orchitis, (12) Sjdgren's syndrome, (13) Osteoporosis (14) Paget's disease.
Connective tissue diseases:
(1) Mixed connective tissue disease, (2) Undifferentiated connective tissue disease (3) Adiposis dolorosa
(4) Systemic lupus erythematosus (SLE), (5) Drug-induced lupus, (6) Adult-onset Still's disease, (7) CREST syndrome, (8) Enteritis-related arthritis, (9) Eosinophilic fasciitis, (10) Felty syndrome, (11) IgG4-related disease (12) Parry-Romberg syndrome, (13) Parsonage-Turner syndrome, (14) Sarcoidosis (15) Schnitzler syndrome, (16) Undifferentiated connective tissue disease (UCTD).
Eye diseases:
(1) Diabetic retinopathy, (2) Autoimmune retinopathy, (3) Autoimmune uveitis, (4) Intermediate uveitis, (5) Dry and wet Age-related Macular Degeneration (AMD), (6) Retinitis Pigmentosa (RP), (7) Ligneous conjunctivitis, (8) Mooren's ulcer, (9) Scleritis, (10) Sympathetic ophthalmia.
Ear Diseases
(1) Autoimmune inner ear disease (AIED).
Pulmonary diseases:
(1) Asthma, (2) Allergic rhinitis (3) Chronic obstructive pulmonary disease (COPD), (4) Autoimmune inner ear disease (AIED).
Gastrointestinal diseases:
(1) Drug-induced liver diseases (2) Autoimmune hepatitis, (3) Inflammatory bowel syndrome, (4) Crohn's disease, (5) Ulcerative colitis (6) Irritable bowel syndrome, (7) Microscopic colitis, (8) Autoimmune enteropathy, (9) Coeliac disease, (10) Gluten intolerance, (11) Lactose intolerance, (12) Plummer-Vinson syndrome, (13); Achalasia, (14) Idiopathic peritonitis.

Diseases of muscles, bone and skin:
(1) Skin immune response following insect bites and stings (2) Contact dermatitis, (3) Polymyositis (4) Myositis, (5) Dermatomyositis, (6) Dermatitis of different causes, (7) Inclusion body myositis, (8) Fibromyalgia, (9) Systemic scleroderma, (10) Psoriasis, (11) Alopecia areata, (12) Autoimmune angioedema, (13) Autoimmune progesterone dermatitis (14) Autoimmune urticarial, (15) Bullous pemphigoid, (16) Cicatricial pemphigoid, (17) Gestational pemphigoid, (18) Dermatitis herpetiformis, (19) Discoid lupus erythematosus (20) Epidermolysis bullosa acquisita, (21) Erythema nodosum, (22) Hidradenitis suppurativa, (23) Lichen planus, (24) Lichen sclerosus, (25) Linear IgA disease (LAD), (26) Morphea (27) Pemphigus vulgaris (28) *Pityriasis*: a. *Pityriasis* alba, b. *Pityriasis* lichenoides chronica, c. *Pityriasis rosea*, d. *Pityriasis* circinata, e. *Pityriasis rubra* pilaris, f. *Pityriasis versicolor*, g. Dandruff, historically called *Pityriasis* capitis, h. *Pityriasis* amiantacea, i. *Pityriasis* lichenoides et varioliformis *acuta* (PLEVA), j. Mucha-Habermann disease, (29) Vitiligo, (30) Angioedema: a. Acquired angioedema, b. Hereditary angioedema, c. Antineurotic oedema (Quincke's oedema), (31) Eczema, (32) Rheumatoid arthritis, (33) Chronic inflammation of the knee joints, hip joints, spine joints, etc., (34) Chronic spondylarthrosis, (35) Chronic osteochondritis and osteoarthritis (36) Juvenile arthritis, (37) Ankylosing spondylitis, (38) Psoriatic arthritis, (39) Palindromic rheumatism, (40) Relapsing polychondritis, (41) Polymyalgia rheumatica, (42) Antisynthetase syndrome.

Urogenital Diseases
(1) Chronic interstitial cystitis (2) Recurrent cystitis, (3) Drug-induced nephropathies, (4) Diabetic nephropathy, (5) Nephrotic syndrome, (6) The nephritic syndrome, (7) Rapidly progressive glomerulonephritis, (8) Acute renal failure, (9) Secondary renal dysfunction.

2. Treatment-Induced Immune-Related Diseases
(1) Radiation-induced encephalopathy, (2) Chemotherapy-related kidney injury: a. Complex renal cysts, b. Interstitial nephritis, c. Renal papillary necrosis, d. Renal infarction, e. Acute tubular necrosis (3) Chemotherapy-related bladder injury: a. Chemotherapy-induced cystitis, b. Haemorrhagic cystitis, (4) Chemotherapy-related gastrointestinal injury: a. Stomatitis, b. Pharyngitis, c. Oesophagopharyngitis, d. Mucositis, e. Oral and anal inflammation or ulceration, f. Bowel necrosis, g. Gastrointestinal ulceration, h. Enteritis, i. Pancreatitis, j. Acute hepatitis.

3. Infectious Diseases
Viral disease:
Hepatitis A, B, C and D (HAV, HBV, HCV and HDV); Human retroviruses; Human immunodeficiency virus (HIV); HTLV-1; Abelson murine leukaemia virus; Rous sarcoma virus; Zika virus (ZiKV); Influenza A and B virus (IAV and IBV); Coronaviruses: MERS, SARS, SARS-CoV-2; Rhinoviruses; Human respiratory syncytial virus; Adenoviruses; Enteroviruses; Human metapneumoviruses; Herpes simplex or zoster encephalitis; Herpes simplex or zoster dermatitis; Herpesvirus type 6, 7 and 8; Dengue virus; West Nile virus; Ebolavirus and Marburgvirus Infections; Hendra virus; Nipa virus; Human papilloma virus (HPV); Epstein-Barr virus (EBV), Infectious mononucleosis; Rubeola: Measles virus; Rubella; Mumps; Smallpox; Chickenpox; Yellow fever; Viral myocarditis; Viral haemorrhagic fever; Rabies; Hand-foot-and-mouth disease; Orf Parapoxvirus; Molluscum contagiosum Scrub typhus; Norovirus; Cytomegalovirus (CMV); Condyloma *acuminatum*; Parvovirus; Arthropod-borne and rodent-borne virus infections.

Bacterial infections:
Cat-scratch disease; Tularemia; Donovanosis; Nocardiosis; Actinomycosis and Whipple's Disease; Typhoid; Leptospirosis; Q fever; Brucellosis; Melioidosis; Echinococcal (hydatid) disease; Chronic osteomyelitis; Lyme disease (*Borrelia burgdorferi*); Tick-borne spotted fevers; Tuberculosis; Buruli ulcer: *Mycobacterium ulcerans*; Cutaneous tuberculosis: *M. tuberculosis*; Leprosy: *M. leprae*; *Helicobacter pylori*; Schistosomiasis; Histoplasmosis; *Entamoeba histolytica*; Giardiasis; Filariasis; Visceral larva migrans; Anthrax: *Bacillus anthracis*; Ulceroglandular tularemia; *Francisella tularensis*; Bubonic plague: *Yersinia pestis*; Chancroid: *Haemophilus ducreyi*; Primary syphilis: *T. pallidum*; Gonococcal Infections; Syphilis; Treponematoses; *Mycoplasma pneumoniae* infections; Chlamydial infections; *C. trachomatis* infections; Meningitis, cerebritis and brain abscess; Bacterial meningitis; Brain abscess, suppurative intracranial infections; Cerebral malaria: *Plasmodium falciparum*; Spinal epidural abscess; Japanese encephalitis; Erysipelas Cellulitis; Folliculitis; Myositis and myonecrosis; Tetanus; *Legionella* infections; Infective gastroenteritis; Pneumonia; Acute respiratory distress syndrome (ARDS); Lung abscess; Infective endocarditis.

Fungal infections: Mycoses
Coccidioidomycosis; Histoplasmosis; Blastomycosis; Phaeohyphomycosis; Penicilliosis; Sporotrichosis; Paracoccidioidomycosis; Candidiasis; Aspergillosis; Cryptococcosis; Mucormycosis (zygomycosis); Scedosporiosis; Trichosporonosis; Fusariosis; Pneumocystosis.

Protozoal infections:
*Entamoeba histolytica*; Malaria: *Plasmodium falciparum*; Babesiosis; Leishmaniasis; Chagas disease and African trypanosomiasis; Toxoplasmosis; Trichomoniasis.

Helmintic infections.

4. Cardiovascular Diseases and Neurovascular Diseases
Brain: (1) Cerebral Autosomal Dominant Arteriopathy with Subcortical Infarcts and Leukoencephalopathy (CADASIL), (2) Ischaemic stroke, (3) Aneurysmal subarachnoid haemorrhage, (4) Cerebral ischaemia following subarachnoid haemorrhage, (5) Cerebral vasospasm; Atherosclerosis; Systemic arterial hypertension; Pulmonary hypertension; Deep venous thrombosis and pulmonary embolism; Heart: (1) Angina pectoris, (2) Myocardial ischaemia, (3) Myocardial infarction, (4) Myocardial stunning, Myocardial hibernation, (5) Post-ischaemic myocardial dysfunction, (6) Ischaemic cardiomyopathy, (7) Atrial and ventricular arrhythmia including atrial fibrillation, (8) Post-myocardial infarction syndrome, (9) Post-pericardiotomy syndrome, (10) Pericarditis, (11) Myocarditis, (12) Rheumatic fever, (13) Cardiac complication after brain damage: a. Stress cardiomyopathy, b. Broken heart syndrome, c. Cardiac dysfunction and arrhythmia after subarachnoid haemorrhage, d. Cardiac dysfunction and arrhythmia after traumatic brain injury.

5. Neuroinflammatory and Neurodegenerative Diseases
Alzheimer's disease; Parkinson's disease; Huntington's disease; Extrapyramidal symptoms: (1) Acute dystonic reactions, (2) Oculogyric crisis, (3) Akathisia, (4) Pseudo-parkinsonism, (5) Tardive dyskinesia, Sydenham's chorea; Acute disseminated encephalomyelitis (ADEM); Hashimoto's encephalopathy; Bickerstaffs encephalitis; Anti-N-Methyl-D-Aspartate (Anti-NMDA) Receptor Encephalitis; Spinocerebellar ataxias; Susac's syndrome; Tolosa-Hunt syndrome; Meniere's disease; Multiple sclerosis; Idiopathic inflammatory demyelinating diseases; Transverse myelitis;

Neuromyelitis optica (Devic's disease); Optic neuritis; Balo concentric sclerosis; Acquired neuropathies: a. Chronic secondary polyneuropathies, b. Chronic inflammatory demyelinating polyneuropathy (CIDP), c. Progressive inflammatory neuropathy, d. Guillain Barre syndrome, e. Critical illness polyneuropathy, f. Acute and chronic motor axonal neuropathy; Hereditary neuropathies: a. Charcot-Marie-Tooth disease type 1, 2 and 3, b. Hereditary neuralgic amyotrophy; Myotonic dystrophy type I and II; Amyotrophic lateral sclerosis (ALS); Neuralgic amyotrophy (Parsonage-Turner Syndrome); Neuromyotonia; Myasthenia gravis; Restless legs syndrome; Stiff-person syndrome.

6. Epileptic Disorders

Generalised epileptic seizures (grand mal) including status epilepticus; Focal epileptic seizures: a. Frontal lobe epilepsy, b. Temporal lobe epilepsy, c. Benign Rolandic epilepsy, d. Benign occipital epilepsy of childhood; Autosomal dominant nocturnal frontal lobe epilepsy; Childhood absence epilepsy; Dravet syndrome; Epilepsy in females with mental retardation; Juvenile myoclonic epilepsy; Lennox-Gastaut syndrome; Febrile infection-related epilepsy syndrome; West syndrome; Ohtahara syndrome; Reflex epilepsies; Progressive myoclonic epilepsies; Rasmussen's encephalitis.

7. Affective Disorders and Psychiatric Syndromes

Schizophrenia; Depression; Bipolar disorder; Occupational burnout; Pediatric Autoimmune Neuropsychiatric Disorder Associated with *Streptococcus* (PANDAS); Attention deficit hyperactivity disorder Posttraumatic stress disorder; Fibromyalgia.

8. Fibrosis

Primary fibrosis:

Interstitial pulmonary fibrosis (ILD); Retroperitoneal fibrosis; Primary biliary cholangitis (primary biliary cirrhosis or primary liver cirrhosis).

Disease-induced fibrosis:

Secondary pulmonary fibrosis; Secondary inflammation due to cystic fibrosis; Primary sclerosing cholangitis; Interstitial bladder fibrosis; Secondary liver cirrhosis: a. Alcoholic cirrhosis, b. Hepatitis C-induced cirrhosis, c. Human immunodeficiency virus-induced cirrhosis, d. Metastatic carcinomatosis cirrhosis.

Cancer-induced fibrosis: Fibrosis formation induced by cancer.

Tumour pseudoprogression: Treatment induced fibrosis mimicking tumour progression especially in neuroendocrine tumours.

Treatment-induced fibrosis:

Fibrosis formation induced by medical, surgical or radioactive treatments, i.e. Post abdominal operation peritoneal fibrosis with or without ileus; Fibrosis following organ transplantation; Chemotherapy-induced chronic gastrointestinal fibrosis.

9. Paraneoplastic Syndromes:

Paraneoplastic cerebellar degeneration; Lambert-Eaton myasthenic syndrome; Paraneoplastic cerebellar degeneration; Encephalomyelitis, limbic encephalitis; Brainstem encephalitis; Opsoclonus myoclonus ataxia syndrome; Anti-NMDA receptor encephalitis; Polymyositis; Acanthosis *nigricans*; Dermatomyositis; Leser-Trelat sign; Necrolytic migratory erythema; Sweet's syndrome; Florid cutaneous papillomatosis; Pyoderma gangrenosum; Acquired generalized hypertrichosis.

10. Cancer and Neoplasms

Immune-related and neoplastic blood diseases:

Aplastic anaemia; Antiphospholipid syndrome (APS, APLS); Thrombotic thrombocytopenic purpura (TTP); Idiopathic thrombocytopenic purpura (ITP); Autoimmune haemolytic anaemia; Autoimmune lymphoproliferative syndrome; Autoimmune neutropenia; Cold agglutinin disease; Essential mixed cryoglobulinemia; Evans syndrome; Pernicious anaemia; Pure red cell aplasia; Thrombocytopenia; Lymphangitis carcinomatosis; Myelodysplastic/myeloproliferative neoplasms (MPN/MPD): (1) Polycythaemia vera, (2) Essential thrombocythemia, (3) Primary myelofibrosis, (4) Fibrotic myelofibrosis, (5) Lymphomas: a. Non-Hodgkin Lymphoma, b. Non-Hodgkin Lymphoma in Children (Burkitt lymphoma), c. Hodgkin Disease, d. Lymphoma of the skin, e. Waldenstrom macroglobulinemia, f. Multiple myeloma (Kahler's disease), g. Primary cerebral lymphoma, (6) Leukaemia: a. Acute myeloid leukaemia, b. Chronic myeloid leukaemia, c. Acute lymphocytic leukaemia, d. Chronic lymphocytic leukaemia, (6) Unclassifiable MPN/MPD.

Solid tumours:

A. Neuroendocrine tumours (NETs)

(1) Pituitary gland: NET of the anterior pituitary, (2) Thyroid gland: Neuroendocrine thyroid tumours and medullary carcinoma, (3) Parathyroid NETs, (4) Thymus and mediastinal carcinoid tumours, (5) Pulmonary NETs: a. Bronchial NETs, b. Pulmonary carcinoid tumours: typical carcinoid and atypical carcinoid, c. Small-cell lung cancer (SCLC), d. Large cell neuroendocrine carcinoma of the lung (LCNEC), e. Extrapulmonary small cell carcinomas (ESCC or EPSCC), (6) Gastroenteropancreatic neuroendocrine tumours (GEP-NET): a. Foregut NETs (stomach, proximal duodenum, thymus, lung and bronchus), b. Pancreatic NETs, c. Midgut GEP-NET (from distal half of 2nd part of the duodenum to the proximal two-thirds of the transverse colon), appendix NETs, e. Hindgut NETs, (7) Liver and gallbladder NETs, (8) Adrenal tumours and adrenomedullary tumours, (9), (10) Pheochromocytoma, (11) Peripheral nervous system NETs: a. Schwannoma, b. Paraganglioma, c. Neuroblastoma, (12) Breast NETs, (13) Genitourinary tract NETs: a. urinary tract carcinoid tumour and neuroendocrine carcinoma, b. ovary NETs, c. NETs of the cervix, d. Prostate NETs, e. Testes NETs, (14) Merkel cell carcinoma of skin (trabecular cancer), (15) Hereditary NETs: a. Multiple endocrine neoplasia type 1 (MEN1) and type 2 (MEN2), b. Von Hippel-Lindau (VHL) disease, c. Neurofibromatosis type 1 and type 2, d. Schwanomatosis, e. Tuberous sclerosis, f. Carney complex (LAMB or NAME syndrome).

B. Central Nervous System Tumours (1) Brain tumours and spinal tumours: a. Metastatic brain tumours, b, Pilocytic astrocytoma, c. Glioma, d. Glioblastoma multiforme (GBM), e. Oligodendroglioma, f. Ependymoma, g. Medulloblastoma, h. Meningeal tumours, i. Meningioma, j. Metastatic meningitis carcinomatosis.

C. Oropharyngeal Tumours:

Benign tumours: Eosinophilic granuloma, Fibroma, Granular cell tumour, Keratoacanthoma, Leiomyoma, Osteochondroma, Lipoma, Schwannoma, Neurofibroma, Papilloma, Condyloma *acuminatum*, Verruciform xanthoma, Pyogenic granuloma, Rhabdomyoma, Odontogenic tumours, Precancerous lesions, Leukoplakia, Erythroplakia, Erythroleukoplakia, Malignant tumours, Squamous cell carcinoma, Verrucous carcinoma, Minor salivary gland carcinomas, Lymphomas.

D. Laryngeal Cancer

Paranasal sinus and nasal cavity cancer, Nasopharynx cancer, Teratomas, Adenocarcinomas, Adenoid cystic carcinomas, Mucoepidermoid carcinomas, Salivary gland cancer, Thyroid cancers: a. Papillary thyroid cancer, b. Non-invasive follicular thyroid neoplasm with papillary-like nuclear features, c. Follicular thyroid cancer, c. Poorly differentiated thyroid cancer, d. Anaplastic thyroid cancer, e. Thyroid lymphoma, f. Squamous cell thyroid carcinoma, g. Sarcoma of thyroid, h. Hurthle cell carcinoma.

E. Skin Cancers

Basal-cell carcinoma, squamous-cell carcinoma, Malignant melanoma, Kaposi sarcoma, F. Cancer of the Vascular System Angiosarcomas, Epithelioid haemangioendotheliomas, Haemangiopericytomas, Lymphangiosarcomas, Kaposiform haemangioendotheliomas (KHEs), Infantile haemangioma, Congenital haemangioma, Haemangioblastoma, Pyogenic granuloma, Tufted angioma, Glomus tumour.

G. Muscle and Bone Tumours

Leiomyoma, Leiomyosarcoma, Smooth muscle tumour of uncertain malignant potential (STUMP), Metastatic tumours, Osteosarcoma, Chondrosarcoma, Ewing's sarcoma, Fibrosarcoma, Undifferentiated pleomorphic sarcoma, Teratomas, Osteoma, Osteoid osteoma, Osteochondroma, Osteoblastoma, Enchondroma, Giant cell tumour of bone, Aneurysmal bone cyst.

H. Breast Cancer

Metastatic tumours, Invasive ductal carcinoma, Invasive lobular carcinoma, Tubular carcinoma, Mucinous (colloid) carcinoma, Carcinomas with medullary features, Invasive papillary carcinoma, Breast lymphoma, Breast sarcoma.

I. Lung Tumours

Metastatic tumours, Bronchial leiomyoma, Primary lung cancers: a. Small-cell lung carcinoma (SCLC), b. Non-small-cell lung carcinoma NSCLC), c. Pleuropulmonary blastoma, d. Lymphomas of the lung, e. Sarcomas of the lung, f. Mediastinal tumours, g. Pleural tumours, h. Malignant mesothelioma, j. Pleural sarcomas, k. Pleural angiosarcoma, I. Pleural desmoplastic small round cell tumour (pleural DSRCT), m. Pleural synovial sarcoma, n. Pleural solitary fibrous tumour (pleural SFT), o. Smooth muscle tumours of the pleura, p. Pleural carcinomas, q. Pleural mucoepidermoid carcinoma, r. Pleural pseudomesotheliomatous adenocarcinoma, s. Pleural calcified fibrous pseudotumour.

J. Gastrointestinal Tumours (1) Krukenberg tumour (metastatic tumour): (2) Oesophageal cancer, a. Squamous-cell carcinoma (ESCC), b. Oesophageal adenocarcinoma (EAC), c. Barrett's oesophagus, d. Gastric cancer, e. Gastric adenocarcinoma, f. Signet ring cell carcinoma, g. Gastric lymphoma, h. Extranodal marginal zone B-cell lymphomas (MALT lymphoma), (2) Carcinoid: a. Duodenal adenocarcinoma, b. Appendix, c. Carcinoid (3) Pseudomyxoma peritonei: a. Colorectal tumours (4) Colorectal polyp: a. adenoma, b. hyperplastic, c. juvenile, d. sessile serrated adenoma, e. traditional serrated adenoma, f. Peutz-Jeghers syndrome, (5) Cronkhite-Canada syndrome, (6) Polyposis syndromes: a. Juvenile MUTYH-associated, familial adenomatous and serrated polyposis, (7) Adenocarcinoma, 8) Familial adenomatous polyposis, (10) Hereditary nonpolyposis colorectal cancer, (11) Anal tumour: Squamous cell carcinoma, (12) Liver cancer, (13) Metastatic tumours, (14) Hepatocellular carcinoma, (15) Hepatoblastoma, (16) Hepatocellular adenoma, (17) Cavernous haemangioma, (18) Focal nodular hyperplasia, (19) Nodular regenerative hyperplasia, (20) Gallbladder cancer, (21) Cholangiocarcinoma, (22) Klatskin tumour, (23) Gallbladder adenocarcinoma, (24) Pancreatic cancer, (25) Exocrine tumours: a. Adenocarcinoma, b. Pancreatic ductal adenocarcinoma, (26) Cystic neoplasms: a. Serous microcystic adenoma, b. Intraductal papillary mucinous neoplasm, c. Mucinous cystic neoplasm, d. Solid pseudopapillary neoplasm, e. Pancreablastoma, (27) Endocrine PanNETs: a. MALT lymphomas, b. Peritoneal tumours, (28) Metastatic peritonitis carcinomatosis.

K. Urogenital Cancers (1) Renal tumours: a. Metastatic tumour, b. Renal cell carcinoma (RCC): b1. Clear cell RCC, b2. Papillary RCC, b. Chromophobe RCC, b4. Collecting duct RCC, c. Clear cell sarcoma, d. Mesoblastic nephroma, e. Wilm's tumour (nephroblastoma), f. Renal oncocytoma, g. Cystic nephroma, h. Angiomyolipoma, i. Metanephric adenoma, j. Renal medullary fibroma, (2) Ureteral cancer: a. Transitional cell carcinoma, b. Ureteral neoplasm, (3) Bladder tumours: a. Metastatic tumours, b. Papillary transitional cell carcinoma, c. Non-papillary transitional cell carcinoma, d. Squamous cell carcinoma, e. Adenocarcinomas, f. Sarcomas, g. Small cell carcinomas, (4) Ovarian tumours, a. Malignant ovarian cancer: a1. Epithelial cancers, a2. Germ cell cancers, a3. Stromal cancers, b. Benign: b1. Surface epithelial tumours, b2. Stromal tumours, b3. Germ cell tumours, (5) Uterine tumours: a. Uterine fibroids or leiomyomas (6) Cervical tumours: a. Cervical cancer, a1. Squamous cell carcinoma, a2. Adenocarcinoma, a3. Adenosquamous carcinoma, a4. Small cell carcinoma, a5. Neuroendocrine tumour, a6. Glassy cell carcinoma, a7. Villoglandular adenocarcinoma, b. Cervical intraepithelial neoplasia, (7) Testicular tumours: a. Germ cell tumours: a1. Intratubular germ cell neoplasia, a2. Seminoma, a3. Spermatocytic tumour, a4. Embryonal carcinoma, a5. Yolk sac tumour, b. Trophoblastic tumours: b1. Choriocarcinoma, b2. Monophasic choriocarcinoma, b3. Placental site trophoblastic tumour, b4. Cystic trophoblastic tumour, c. Teratomas: c1. Dermoid cyst, c2. Epidermoid cyst, c3. Monodermal teratoma (Carcinoid), c4. Primitive neuroectodermal tumour (PNET), c5. Nephroblastoma-like tumour, c6. Teratomic tumour with somatic-type malignancy, d. Sex cord—gonadal stromal tumours: d1. Leydig cell tumour, d2. Sertoli cell tumour, d3. Lipid rich variant, d4. Sclerosing variant, d5. Large cell calcifying variant, d6. Intratubular Sertoli cell neoplasia in Peutz-Jeghers syndrome, d7. Granulosa cell tumour, d8. Adult type, d9. Juvenile type, d10. Thecoma fibroma group, d11. Thecoma, d12. Fibroma, d13. Incompletely differentiated tumours, d14. Mixed types tumours, e. Mixed germ cell and sex cord/gonadal stromal tumours: e1. Gonadoblastoma, e2. Germ cell-sex cord/gonadal stromal tumour, unclassified, f. Miscellaneous tumours of the testis: f1. Lymphomas: f1a. Primary testicular diffuse large B-cell lymphoma, f1b. Mantle cell lymphoma of the testes, f1c. Extranodal marginal zone B cell lymphoma of the testes, f1d. Extranodal NK/T-cell lymphoma, nasal type of the testes, f1e. Peripheral T-cell lymphoma of the testes, fif. Activin receptor-like kinase-1-negative anaplastic large cell lymphoma of the testes, f1g. Paediatric-type follicular lymphoma of the testes, f2. Carcinoid, f3. Tumours of ovarian epithelial types: f3a. Serous tumour of borderline malignancy, f3b. Serous carcinoma, f3c. Well differentiated endometrioid tumour, f3d. Mucinous cystadenoma, f3e. Mucinous cystadenocarcinoma, f3f. Brenner tumour, f4. Nephroblastoma. f5. Paraganglioma, g. Haematopoietic tumours, h. Tumours of collecting ducts and rete: h1. Adenoma, h2. Carcinoma, i. Tumours of the paratesticular structures: i1 Adenomatous tumour, i2 Malignant and benign mesothelioma, i3. Adenocarcinoma of the epididymis, i4. Papillary cystadenoma of the epididymis, i5. Melanotic neuroectodermal tumour, i6. Desmoplastic small round cell tumour, j. Mesenchymal tumours of the spermatic cord and testicular adnexae: j1. Lipoma. J2. Liposarcoma, j3. Rhabdomyosarcoma, j4. Aggressive angiomyxoma, j5. Angiomyofibroblastoma-like tumour (see myxoma), j6. Fibromatosis, j7. Fibroma, j8. Solitary fibrous tumour, j9. Others, k. Secondary tumours of the testis, (8) Urethral cancer: a. Transitional cell carcinoma, b. Squamous-cell carcinoma, c. Adenocarcinoma, d. Melanoma, e. Prostate tumours, f. Metastatic prostate tumour, g. Benign prostatic hyperplasia, i. Prostate cancer, (9) Penile tumours: a. Phimosis, b. Penile cancer.

L. Retroperitoneal Tumours (1) Solid tumours: a. Metastatic tumour, b. Fibroma, fibrosarcoma, malignant fibrous histiocytoma, c. Lipoma, liposarcoma, d. Leiomyoma, leiomyosarcoma, e. Desmoid tumours. e. Ganglioneuroma, ganglioneuroblastoma, f. Schwannoma, neurofibroma, g. Extragonadal germ cell tumour, h. Lymphoma, i. Lymphadenopathy, (2) Cystic tumours, a. Cystic lymphangioma, b. Cystic teratoma, c. Cystadenoma, cystadenocarcinoma, d. Cystic mesothelioma. e. Epidermoid cyst, f. Tarlov cyst (perineural cyst).

11. Trauma and Posttraumatic Syndromes (1) Traumatic subarachnoid haemorrhage, (2) Head injury including severe traumatic head injury, (3) Cerebral ischaemia following traumatic brain injury, (4) Polytrauma condition, (5) Postraumatic epileptic seizures.

12. Inflammation after Organ Transplantation of Lung, Kidney, Heart, Liver, Etc.

(1) Acute immune reaction after organ transplantation, (2) Chronic organ tissue rejection reaction by the host, (3) Fibrosis following organ transplantation.

The invention claimed is:

1. A method for the treatment of a hyperinflammatory syndrome in a mammalian patient, comprising primary lymph node targeted administration of a mammalian P2X7 receptor (P2X7R) antagonist to the said patient to a concentration in the said targeted lymph nodes that is above the maximal tolerable plasma level of the said antagonist in the said mammal, wherein said P2X7R antagonist is delivered directly from the administration site to the lymph node, the administration being a bolus dosage corresponding with at least 1,000 times of the amount of the P2X7R antagonist comprised in 1 ml plasma at the maximum tolerable plasma level of the P2X7R antagonist.

2. The method according to claim 1, wherein the P2X7R antagonist is chosen from the group consisting of aminoamide derivatives, in particular lidocaine, bupivacaine, ropivacaine and mepivacaine; antibodies against P2X7Rs, in particular monoclonal antibodies, aminoester derivatives, in particular benzocaine and procaine; adamantane amide derivatives; triazole derivatives; diarylimidazolidine derivatives; pyroglutamic acid amide derivatives; pyrazole acetamide derivatives; dihydrodibenzo [a,g]quinolizinium derivatives; tetrazole derivatives; tyrosine based derivatives; pyrazolodiazepine derivatives; imidazoles derivatives; benzamides derivatives, KN62 analogues and derivatives; adamantane carboxamides; aryl carbohydrazides; cyanoguanidines; aryltetrazoles and aryltriazoles; PPADS tetrasodium salt; brilliant blue G (BBG); oxidised ATP (o-ATP); massadine; stylissadine A and B; P2X7R inhibitors C23, C40 and C60; [3H]A-804598 ([3H]2-cyano-1-[(1 S)-1-phenylethyl]-3-quinolin-5-ylguanidine); and bicycloheteroaryl compounds.

3. The method according to claim 1, wherein the P2X7R antagonist is administered in a liquid medium comprising at least 1 w/v % of the P2X7R antagonist.

4. The method according to claim 1, wherein the lipophilic P2X7R antagonist is in the form of the free base thereof, the hydrophilic P2X7R antagonist lidocaine being in the form of a water soluble pharmaceutically acceptable salt thereof.

5. The method according to claim 1, wherein the administration is an immediate release dosage form or a sustained release dosage form.

6. The method according to claim 1, wherein the bolus dosage corresponds with at least 5,000 times the amount of the P2X7 receptor antagonist, that is comprised in 1 ml plasma at the maximal tolerable plasma level of the said antagonist, preferably at least 10,000.

7. The method according to claim 6, wherein the bolus is administered 2-10 times daily.

8. The method according to claim 1, wherein the P2X7R antagonist is administered in a liquid medium comprising at least 2.5 w/v % of the P2X7R antagonist.

9. The method according to claim 1, wherein the P2X7R antagonist is in its free base form and is administered in a liquid medium comprising at least 5 w/v % of the P2X7R antagonist.

10. The method according to claim 1, wherein the P2X7R antagonist is lidocaine.

11. The method according to claim 1, wherein the hyperinflammatory syndrome is of a disease being chosen from the group consisting of COVID-19, sepsis, polymyalgia rheumatica, psoriatic arthritis, spondylarthrosis, chronic interstitial cystitis, chronic inflammatory bladder condition, knee arthrosis, multiple sclerosis, systemic inflammatory response syndrome (SIRS) and renal dysfunction in advance cancers, amyotrophic lateral sclerosis, Alzheimer's disease, idiopathic Parkinson's disease, diabetic polyneuropathy, myasthenia gravis, chronic obstructive pulmonary disease (COPD), Graves' disease, ulcerative colitis, inflammatory bowel disease, allergic reaction to processionary caterpillar toxin, rheumatoid arthritis, ischaemic cardiomyopathy in a patient with diabetes mellitus, acute lumbago, systemic lupus erythematosus (SLE), and dyspnoea.

12. The method according to claim 11, wherein the disease is dyspnoea associated with a viral infection, bacterial infection, carcinomas, chronic obstructive pulmonary disease (COPD), asthma, allergy, or chemotherapy.

13. The method according to claim 12, wherein the dyspnoea is associated with a viral infection caused by a virus, chosen from the group consisting of coronavirus, in particular SARS-CoV-2; influenza; ebola; respiratory syncytial virus; and HIV.

14. A method for the treatment of a hyperinflammatory syndrome in a mammalian patient, comprising primary lymph node targeted administration of a mammalian P2X7 receptor (P2X7R) antagonist to the said patient to a concentration in the said targeted lymph nodes that is above the maximal tolerable plasma level of the said antagonist in the said mammal, wherein the disease is dyspnoea associated with a viral infection.

15. The method according to claim 14, wherein the P2X7R antagonist is chosen from the group consisting of aminoamide derivatives, in particular lidocaine, bupivacaine, ropivacaine and mepivacaine; antibodies against P2X7Rs, in particular monoclonal antibodies, aminoesterderivatives, in particular benzocaine and procaine; adamantane amide derivatives; triazole derivatives; diarylimidazolidine derivatives; pyroglutamic acid amide derivatives; pyrazole acetamide derivatives; dihydrodibenzo [a,g]quinolizinium derivatives; tetrazole derivatives; tyrosine based derivatives; pyrazolodiazepine derivatives; imidazoles derivatives; benzamides derivatives, KN62 analogues and derivatives; adamantane carboxamides; aryl carbohydrazides; cyanoguanidines; aryltetrazoles and aryltriazoles; PPADS tetrasodium salt; brilliant blue G (BBG); oxidised ATP (o-ATP); massadine; stylissadine A and B; P2X7R inhibitors C23, C40 and C60; [3H]A-804598 ([3H]2-cyano-1-[(1 S)-1-phenylethyl]-3-quinolin-5-ylguanidine); and bicycloheteroaryl compounds.

16. A method according to claim 14, wherein said P2X7R antagonist is delivered directly from the administration site to the lymph node, the administration being selected from the group consisting of:
  transmucosal and transdermal administration of the P2X7R antagonist being administered in lipophilic form, and/or
  invasive administration chosen from intradermal and subcutaneous, including subdermal, administration, the P2X7R antagonist being in hydrophilic form;
  wherein said administration is chosen from:
  a bolus dosage corresponding with at least 1,000 times of the amount of the P2X7R antagonist comprised in 1 ml plasma at the maximum tolerable plasma level of the P2X7R antagonist, and
  continuous administration of the P2X7R antagonist, the dosage corresponding with at least 10 times the $IC_{10}$ value for the P2X7R antagonist per kg body weight per hour.

17. The method according to claim 16, wherein the P2X7R antagonist is administered in a liquid medium comprising at least 1 w/v % of the P2X7R antagonist.

18. The method according to claim 16, wherein the lymph node targeted administration comprises transmucosal administration in the oral cavity.

19. The method according to claim 18, wherein the administration is buccal, sublingual, or a combination thereof.

20. The method according to claim 16, wherein the lipophilic P2X7R antagonist is in the form of the free base thereof, the hydrophilic P2X7R antagonist lidocaine being in the form of a water soluble pharmaceutically acceptable salt thereof.

21. The method according to claim 16, wherein the P2X7R antagonist is administered by continuous infusion to a concentration in the targeted lymph nodes that corresponds to the $IC_x$ for the P2X7 receptor, the said $IC_x$ being above the maximal tolerable plasma level of the said antagonist in the said mammal, wherein ≥10, preferably ≥20, more preferably ≥30, even more preferably ≥40 and most preferably about 50.

22. The method according to claim 16, wherein the administration is an immediate release dosage form or a sustained release dosage form.

23. The method according to claim 16, wherein the administration is by bolus dosage, wherein the bolus dosage corresponds with at least 5,000 times the amount of the P2X7 receptor antagonist, that is comprised in 1 ml plasma at the maximal tolerable plasma level of the said antagonist, preferably at least 10,000.

24. The method according to claim 23, wherein the bolus is administered 2-10 times daily.

25. The method according to claim 16, wherein the P2X7R antagonist is administered in a liquid medium comprising at least 2.5 w/v % of the P2X7R antagonist.

26. The method according to claim 16, wherein the P2X7R antagonist is in its free base form and is administered in a liquid medium comprising at least 5 w/v % of the P2X7R antagonist.

27. The method according to claim 16, wherein the P2X7R antagonist is lidocaine.

28. The method according to claim 14, wherein the dyspnoea is associated with a viral infection caused by a virus, chosen from the group consisting of coronavirus, in particular SARS-CoV-2; influenza; ebola; respiratory syncytial virus; and HIV.

29. The method according to claim 16, wherein the treatment comprises topical administration of lidocaine in the free base form.

30. The method according to claim 16, wherein the treatment comprises administration of the P2X7R antagonist in its free base form in the oral cavity.

31. The method according to claim 16, wherein the treatment comprises invasive administration of the P2X7R antagonist in a water-soluble salt form, in particular the HCl salt thereof, the invasive administration being by continuous intradermal or subdermal infusion.

* * * * *